United States Patent [19]
Au-Young et al.

[11] Patent Number: 5,817,479
[45] Date of Patent: Oct. 6, 1998

[54] HUMAN KINASE HOMOLOGS

[75] Inventors: Janice Au-Young, Berkeley; Olga Bandman; Phillip R. Hawkins, both of Mountain View; Craig G. Wilde, Sunnyvale, all of Calif.

[73] Assignee: Incyte Pharmaceuticals, Inc., Palo Alto, Calif.

[21] Appl. No.: 700,575

[22] Filed: Aug. 7, 1996

[51] Int. Cl.$^6$ .............................. C12P 21/06; C12N 15/64
[52] U.S. Cl. .................... 435/69.1; 435/91.4; 435/320.1; 435/325; 435/252.1; 536/23.2; 536/23.5
[58] Field of Search .................................. 536/23.1, 23.2, 536/23.5; 435/91.4, 325, 320.1, 69.1, 252.1

[56] References Cited

PUBLICATIONS

Taniguchi, "Cytokine Signaling Through Nonreceptor Protein Tyrosine Kinases," *Science*, 268:251–55 (14 Apr. 1995).
Egan et al., "The pathway to signal achievement," *Nature*, 365:781–783.
Derijard et al., "Independent Human MAP Kinase Signal Transduction Pathways Defined by MEK and MKK Isoforms," *Science*, 267:682–686 (3 Feb. 1995).
R. Davis, "MAPKs: new JNK expands the group," *TIBS*, 19:470–473 (1994).
Han et al., "A MAP Kinase Targeted by Endotoxin and Hyperosmolarity in Mammalian Cells," *Science*, 265:808–811 (1994).
Levitzki et al., "Tyrosine Kinase Inhibition: An Approach to Drug Development," *Science*, 267:1782–1788 (Mar. 24, 1995).
Stroberg, "Functional expression of receptors in microorganisms," *Trends in Pharmacol.*, 13(3)95–98.
Hanes et al. Gen Bank J. Mol. Biol. 244: 665–672, 1994.
Hanes et al. (1994) J. Mol. Biol. 244, 665–672.
Tamagnone et al. (1994) Oncogene 9(12), 3683–3688.
Bennett et al. (1994) J. Biol. Chem. 269(19), 14211–14218.

*Primary Examiner*—Frank C. Eisenschenk
*Assistant Examiner*—Patrick J. Nolan
*Attorney, Agent, or Firm*—Lucy J. Billings; Sheela Mohan-Peterson; Incyte Pharmaceuticals, Inc.

[57] ABSTRACT

The present invention provides polynucleotides (kin) which identify and encode novel protein kinases (KIN) expressed in various human cells and tissues. The present invention also provides for antisense sequences and oligonucleotides designed from the nucleotide sequences or their complements. The invention further provides genetically engineered expression vectors and host cells for the production of purified KIN peptides, antibodies capable of binding KIN, and inhibitors specifically bind KIN. The invention specifically provides for diagnostic kits and assays which identify a disorder or disease with altered kinase expression and allow monitoring of patients during drug therapy. These assays utilize oligonucleotides or antibodies produced using the kin polynucleotides.

4 Claims, No Drawings

HUMAN KINASE HOMOLOGS

FIELD OF THE INVENTION

The present invention is in the field of molecular biology; more particularly, the present invention describes nucleic acid sequences for novel human kinase homologs.

BACKGROUND OF THE INVENTION

Kinases regulate many different cell proliferation, differentiation, and signalling processes by adding phosphate groups to proteins. Uncontrolled signalling has been implicated in inflammation, oncogenesis, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate which drives activation is generally transferred from adenosine triphosphate molecules (ATP) to a particular protein by protein kinases and removed from that protein by protein phosphatases.

Phosphorylation occurs in response to extracellular signals (hormones, neurotransmitters, growth and differentiation factors, etc), cell cycle checkpoints, and environmental or nutritional stresses and is roughly analogous to the turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein family, a superfamily of enzymes with widely varied functions and specificities. They are usually named after their substrate, their regulatory molecules, after some aspect of a mutant phenotype or arbitrarily. Almost all kinases contain a similar 250–300 amino acid catalytic domain. The N-terminal domain, which contains subdomains I–IV, generally folds into a two-lobed structure and binds and orients the ATP (or GTP) donor molecule. The larger C terminal lobe, which contains subdomains VIA–XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 12 subdomains. The following residues are relatively (~95%) invariant: $G_{50}$ and $G_{52}$ in subdomain I, $K_{72}$ in subdomain II, $G_{91}$ in subdomain III, $E_{208}$ in subdomain VIII, $D_{220}$ and $G_{225}$ in subdomain IX, and the motifs or patterns of amino acids in subdomains VIB, VIII and IX (Hardie G. and Hanks S. (1995) *The Protein Kinase Facts Books*, I and II, Academic Press, San Diego, Calif.).

The cyclin dependent protein kinase (cdk) family includes proteins which are turned on and off as the cell proceeds through the cell cycle. A cdk is active as a kinase only when it is bound to a cyclin. Cdk activation simultaneously requires both the addition of a high energy phosphate to a threonine residue by a kinase and the removal of a covalently-bound phosphate from a specific tyrosine residue by a phosphatase. The concentration of some cyclins rises gradually through a particular part of the cell cycle until their targeted proteolysis ends the coordinated interaction among the cyclin, kinase, and phosphatase molecules.

The second-messenger dependent protein kinases primarily mediate the effects of second messengers such as cyclic AMP (cAMP) cyclic GMP, inositol triphosphate, phosphatidylinositol, 3,4,5-triphosphate, cyclic ADPribose, arachidonic acid and diacylglycerol. For purposes of example, the structure and function of cyclic AMP-dependent protein kinase (A-kinase) will be described. Mammalian cells generally contain at least two forms of A-kinase; type 1 which is cytosolic, and type 2 which is bound to plasma membrane, nuclear membrane or microtubules. In its inactive state, A-kinase consists of a complex of two catalytic subunits and two regulatory subunits. When each regulatory subunit has bound two molecules of cAMP, the catalytic subunit is activated and can transfer a high energy phosphate from ATP to the serine or threonine of a substrate protein. Substrate proteins are usually marked by the presence of two or more basic amino acids on their amino terminal sides. A-kinase is important in metabolism of glycogen, for inactivation of phosphatase inhibitor protein, in transcription of genes which contain a regulatory region called the cAMP response element (CRE), and in regulation of the ion channels of olfactory neurons.

Protein kinase C (PKC) is a water-soluble, $Ca^{++}$-dependent kinase, commonly found in brain tissue, which moves to the plasma membrane in the presence of $Ca^{++}$ ions. Approximately half of the known isoforms of PKC are activated initially by diacylglycerol and phosphatidylserine. Prolonged activation of PKC depends on continued production of diacyglycerol molecules which are formed when phospholipases cleave phosphatidylcholine. In nerve cells, PKC phosphorylates ion channels and alters the excitability of the cell membrane. In other cells, activation of PKC increases gene transcription either by triggering a protein kinase cascade which activates a regulatory element (much like CRE above) or by phosphorylating and deactivating an inhibitor of the regulatory protein.

$Ca^{++}$/calmodulin-dependent protein kinases (CaM-kinases) mediate most of the actions of $Ca^{++}$ in human cells. The CaM-kinases include enzymes with narrow substrate specificity such as myosin light chain kinase which activates smooth muscle contraction and phosphorylase kinase which activates glycogen breakdown and the multifunctional enzyme, CaM-kinase II which is found in all cells. Phosphorylase kinase has four subunits: γ is the catalytic moiety and α, β and ☐δ are regulatory. Since subunits α and β are phosphorylated by A-kinase and subunit ☐δ is $Ca^{++}$/calmodulin, glycogen breakdown can be activated by either cAMP or $Ca^{++}$.

CaM-kinase II is particularly enriched in catecholamine synapses. In those neurons, $Ca^{++}$ influx stimulates both the release of dopamine, noradrenaline or adrenaline and also their resynthesis through the activation of CaM-kinase II. Although the main role of CaM-kinase II is phosphorylation of tyrosine hydroxylase, the rate-limiting enzyme of catecholamine synthesis, CaM-kinase II also autophosphorylates and remains active until phosphotases overwhelm it.

Transmembrane protein-tyrosine kinases are receptors for most growth factors. The first characterized receptor for epidermal growth factor (EGF) is a single pass transmembrane protein of about 1200 amino acids with an extracellular glycosylated portion that interacts with the 53 amino acid EGF molecule. Binding activates the transfer of a phosphate group from ATP to selected tyrosine side chains of the receptor and other specific proteins. Other protein receptors with similar structure include the following growth and differentiation factors (GF)—platelet derived GF, fibroblast GF, hepatocyte GF, insulin and insulin-like GFs, nerve GF, vascular endothelial GF, macrophage colony stimulating factor, etc. Each protein phosphorylates itself by receptor dimerization to initiate the intracellular signalling cascade.

Many protein-tyrosine kinases lack transmembrane regions and form a complex with the intercellular regions of other cell surface receptors. The best known NR-PTKs are the Src kinase family (Src, Yes, Fgr, Fyn, Lck, Lyn, Hck, Blk, etc) and the Janus kinase family (Jak1, Jak2, Jak3, Tyk2, etc). The Src PTKs are located on the cytoplasmic side of the plasma membrane and are characterized by Src homology regions 2 and 3 (SH2 and SH3). Src PTKs recognize short peptide motifs bearing phosphotyrosine or proline residues, respectively, and mediate protein-protein interactions that regulate a whole range of intracellular signalling molecules. Janus PTKs contain PTK or PTK-like domains and interact with growth hormone, prolactin, and some of the same cytokine receptors as Src PTKs. The cytokine receptors are unique both in their ability to recruit multiple PTKs and in the diversity of their intracellular domains which allow flexibility in their responses within different cell types (Taniguchi T. (1995) Science 268:251–55). Src and Jak kinases were first identified as the products of mutant oncogenes in cancer cells where their activation was no longer subject to normal cellular controls.

Extracellular signalling proteins such as transforming growth factor-β (TGF-β), activins, bone morphogenetic protein, and related members of the TGF-β superfamily interact with receptor serine/threonine kinases. Like EGF above, these receptor kinases have a single pass transmembrane domain with a serine/threonine kinase residue on the cytosolic side of the plasma membrane. The signalling pathways which are activated by binding the extracellular signalling molecules are presently under investigation.

Mitogen-activated protein (MAP) kinases also regulate intracellular signalling pathways. They mediate signal transduction from cell surface to nuclei via phosphorylation cascades. Several subgroups have been identified, and each manifests different substrate specificities and responds to distinct extracellular stimuli (Egan S. E. and Weinberg R. A. (1993) Nature 365:781–783).

MAP kinase signalling pathways are present in mammalian cells as well as in yeast. The extracellular stimuli which activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1). In *Saccharomyces cerevisiae*, exposure to mating pheromone or hyperosmolar environments activate the various MAP kinase signalling pathways.

Mammalian cells have at least three subgroups of MAP kinases (Derijard B. et al (1995) Science 267:682–5), each distinguished by a tripeptide motif. They are extracellular signal-regulated protein kinases (ERK) characterized by Thr-Glu-Tyr; c-Jun amino-terminal kinases (JNK) characterized by Thr-Pro-Tyr; and p38 kinase characterized by Thr-Gly-Tyr. Each subgroup is activated by dual phosphorylation of threonine and tyrosine residues by MAP kinase kinases located upstream of the phosphorylation cascade. Activated MAP kinases, in turn, phosphorylate downstream effectors ultimately leading to intracellular changes.

The ERK signal transduction pathway is activated via tyrosine kinase receptors on the plasmalemma. When growth factors bind to tyrosine, they bind to noncatalytic, Src homology (SH) adaptor proteins (SH2-SH3-SH2) and a guanine nucleotide releasing protein (GNRP). GNRP reduces GTP and activates Ras proteins, members of the large family of guanine nucleotide binding proteins (G-proteins). Activated Ras proteins bind to a protein kinase C-Raf-1 and activate the Raf-1 proteins. The activated Raf-1 kinase subsequently phosphorylates MAP kinase kinase (MKK) which, in turn, activate ERKs.

ERKs are proline-directed protein kinases which phosphorylate Ser/Thr-Pro motifs. In fact, cytoplasmic phospholipase A2 (cPLA2) and transcription factor Elk-1 are substrates of ERKs. The ERKs phosphorylate $Ser_{505}$ of cPLA2 thereby increasing its enzymatic activity and resulting in release of arachidonic acid and the formation of lysophospholipids from membrane phospholipids. Likewise, phosphorylation of the transcription factor Elk-1 by ERK ultimately increases transcriptional activity.

JNK is distantly related to the ERK and is similarly activated by dual phosphorylation of Thr and Tyr and by MKK4 (Davis R (1994) TIBS 19:470–473). The JNK signal transduction pathway is also initiated by ultraviolet light, osmotic stress, and the pro-inflammatory cytokines, TNF and IL-1. Phosphorylation of $Ser_{63}$ and $Ser_{73}$ in the $NH_2$-terminal domain of the transcription factor c-Jun increases transcriptional activity.

p38 is a 41 kD protein containing 360-amino acids. Its dual phosphorylation is activated by the MKK3 and MKK4, heat shock, hyperosmolar medium, IL-1 or LPS endotoxin (Han J. et al (1994) Science 265:808–811). Sepsis produced by LPS is characterized by fever, chills, tachypnea, and tachycardia, and severe cases may result in septic shock which includes hypotension and multiple organ failure.

Cells respond to LPS as a stress signal because it alters normal cellular processes and induces the release of systemic mediators such as TNF. CD14 is a glycosylphosphatidyl-inositol-anchored membrane glycoprotein which serves as a LPS receptor on the plasmalemma of monocytic cells. The binding of LPS to CD14 causes rapid protein tyrosine phosphorylation of the 44- and 42-/40-kD isoforms of MAP kinases. Although they bind LPS, these MAP kinase isoforms do not appear to belong to the p38 subgroup.

An detailed understanding of kinase pathways and signal transduction is beginning to reveal some mechanisms for interceding in the progression of inflammatory illnesses and of uncontrolled cell proliferation. The cDNAs, oligonucleotides, peptides and antibodies for the human kinases, which are the subject of this invention and are listed in Table 1, provide a plurality of tools for studying signalling cascades in various cells and tissues and for diagnosing and selecting inhibitors or drugs with the potential to intervene in various disorders or diseases in which altered kinase expression is implicated. The disorders or diseases include, but not limited to, human X-linked agammaglobulinemia, nonspherocytic hemolytic anemia, atherosclerosis, carcinomas (breast, ovary, renal, squamous cell and prostate), diabetes, gliomas, glomerular disease, hepatomegaly, Karposi's sarcoma, lymphoblastic and myelogenous leukemias, myoglobinuria, peptic ulcer disease, psoriasis, pulmonary fibrosis, restenosis, and septic shock due to cholera, *Clostridium difficile, E. coli* and Shigella (Isselbacher K. J. et al (1994) Harrison's Principles of Internal Medicine, McGraw-Hill, New York City; Levitzki A. and A. Gazit (1995) Science 267:1782–88).

SUMMARY OF THE INVENTION

The subject invention provides unique polynucleotides (SEQ ID NOs 1–44) which have been identified as novel human kinases (kin). These partial cDNAs were identified among the polynucleotides which comprise various Incyte cDNA libraries.

The invention comprises polynucleotides which are complementary to the kin sequences (SEQ ID Nos 1–44).

The invention also comprises the use of kin sequences to identify and obtain a full length human kinase cDNAs such as SEQ ID NO 45.

The invention further comprises the use of oligomers from these kin sequences in a kinases kit which can be used to identify a disorder or disease with altered kinase expression and provide a method for monitoring progress of a patient during drug therapy.

Aspects of the invention include use of kin sequences or recombinant nucleic acids derived from them to produce purified peptides. Still further aspects of the invention use these purified peptides to identify antibodies or other molecules with inhibitory activity toward a particular kinase, group of kinases or disease.

In addition, the invention comprises the use of kin specific antibodies in assays to identify a disorder or disease with altered kinase expression and provides a method to monitor the progress of a patient during drug therapy.

DESCRIPTION OF THE FIGURE

FIGS. 1A and 1B display the full length nucleotide sequence for human MAP kinase from stomach tissue (SEQ ID NO 45; Incyte Clone 214915E) and its predicted amino acid sequence.

DETAILED DESCRIPTION OF THE INVENTION

Definitions

As used herein, the abbreviation for kinase in lower case (kin) refers to a gene, cDNA, RNA or nucleic acid sequence while the upper case version (KIN) refers to a protein, polypeptide, peptide, oligopeptide, or amino acid sequence.

An "oligonucleotide" or "oligomer" is a stretch of nucleotide residues which has a sufficient number of bases to be used in a polymerase chain reaction (PCR). These short sequences are based on (or designed from) genomic or cDNA sequences and are used to amplify, confirm, or reveal the presence of an identical, similar or complementary DNA or RNA in a particular cell or tissue. Oligonucleotides or oligomers comprise portions of a DNA sequence having at least about 10 nucleotides and as many as about 50 nucleotides, preferably about 15 to 30 nucleotides. They are chemically synthesized and may be used as probes.

"Probes" are nucleic acid sequences of variable length, preferably between at least about 10 and as many as about 6,000 nucleotides, depending on use. They are used in the detection of identical, similar, or complementary nucleic acid sequences. Longer length probes are usually obtained from a natural or recombinant source, are highly specific and much slower to hybridize than oligomers. They may be single- or double-stranded and carefully designed to have specificity in PCR, hybridization membrane-based, or ELISA-like technologies.

"Reporter" molecules are chemical moieties used for labelling a nucleic or amino acid sequence. They include, but are not limited to, radionuclides, enzymes, fluorescent, chemi-luminescent, or chromogenic agents. Reporter molecules associate with, establish the presence of, and may allow quantification of a particular nucleic or amino acid sequence.

A "portion" or "fragment" of a polynucleotide or nucleic acid comprises all or any part of the nucleotide sequence having fewer nucleotides than about 6 kb, preferably fewer than about 1 kb which can be used as a probe. Such probes may be labelled with reporter molecules using nick translation, Klenow fill-in reaction, PCR or other methods well known in the art. After pretesting to optimize reaction conditions and to eliminate false positives, nucleic acid probes may be used in Southern, northern or in situ hybridizations to determine whether DNA or RNA encoding the protein is present in a biological sample, cell type, tissue, organ or organism.

"Recombinant nucleotide variants" are polynucleotides which encode a protein. They may be synthesized by making use of the "redundancy" in the genetic code. Various codon substitutions, such as the silent changes which produce specific restriction sites or codon usage-specific mutations, may be introduced to optimize cloning into a plasmid or viral vector or expression in a particular prokaryotic or eukaryotic host system, respectively.

"Linkers" are synthesized palindromic nucleotide sequences which create internal restriction endonuclease sites for ease of cloning the genetic material of choice into various vectors. "Polylinkers" are engineered to include multiple restriction enzyme sites and provide for the use of both those enzymes which leave 5' and 3' overhangs such as BamHI, EcoRI, PstI, KpnI and Hind III or which provide a blunt end such as EcoRV, SnaBI and StuI.

"Control elements" or "regulatory sequences" are those nontranslated regions of the gene or DNA such as enhancers, promoters, introns and 3' untranslated regions which interact with cellular proteins to carry out replication, transcription, and translation. They may occur as boundary sequences or even split the gene. They function at the molecular level and along with regulatory genes are very important in development, growth, differentiation and aging processes.

"Chimeric" molecules are polynucleotides or polypeptides which are created by combining one or more of nucleotide sequences of this invention (or their parts) with additional nucleic acid sequence(s). Such combined sequences may be introduced into an appropriate vector and expressed to give rise to a chimeric polypeptide which may be expected to be different from the native molecule in one or more of the following kinase characteristics: cellular location, distribution, ligand-binding affinities, interchain affinities, degradation/turnover rate, signalling, etc.

"Active" is that state which is capable of being useful or of carrying out some role. It specifically refers to those forms, fragments, or domains of an amino acid sequence which display the biologic and/or immunogenic activity characteristic of the naturally occurring kinase.

"Naturally occurring KIN" refers to a polypeptide produced by cells which have not been genetically engineered or which have been genetically engineered to produce the same sequence as that naturally produced. Specifically contemplated are various polypeptides which arise from post-transnational modifications. Such modifications of the polypeptide include but are not limited to acetylation, carboxylation, glycosylation, phosphorylation, lipidation and acylation.

"Derivative" refers to those polypeptides which have been chemically modified by such techniques as ubiquitination, labelling (see above), pegylation (derivatization with polyethylene glycol), and chemical insertion or substitution of amino acids such as ornithine which do not normally occur in human proteins.

"Recombinant polypeptide variant" refers to any polypeptide which differs from naturally occurring KIN by amino acid insertions, deletions and/or substitutions, created using recombinant DNA techniques. Guidance in determining which amino acid residues may be replaced, added or deleted without abolishing characteristics of interest may be found by comparing the sequence of KIN with that of related polypeptides and minimizing the number of amino acid sequence changes made in highly conserved regions.

Amino acid "substitutions" are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid "insertions" or "deletions" are changes to or within an amino acid sequence. They typically fall in the range of about 1 to 5 amino acids. The variation allowed in a particular amino acid sequence may be experimentally determined by producing the peptide synthetically or by systematically making insertions, deletions, or substitutions of nucleotides in the kin sequence using recombinant DNA techniques.

A "signal or leader sequence" is a short amino acid sequence which or can be used, when desired, to direct the polypeptide through a membrane of a cell. Such a sequence may be naturally present on the polypeptides of the present invention or provided from heterologous sources by recombinant DNA techniques.

An "oligopeptide" is a short stretch of amino acid residues and may be expressed from an oligonucleotide. It may be functionally equivalent to and either the same length as or considerably shorter than a "fragment ", "portion ", or "segment" of a polypeptide. Such sequences comprise a stretch of amino acid residues of at least about 5 amino acids and often about 17 or more amino acids, typically at least about 9 to 13 amino acids, and of sufficient length to display biologic and/or immunogenic activity.

An "inhibitor" is a substance which retards or prevents a chemical or physiological reaction or response. Common inhibitors include but are not limited to antisense molecules, antibodies, antagonists and their derivatives.

A "standard" is a quantitative or qualitative measurement for comparison. Preferably, it is based on a statistically appropriate number of samples and is created to use as a basis of comparison when performing diagnostic assays, running clinical trials, or following patient treatment profiles. The samples of a particular standard may be normal or similarly abnormal.

"Animal" as used herein may be defined to include human, domestic (cats, dogs, etc), agricultural (cows, horses, sheep, goats, chicken, fish, etc) or test species (frogs, mice, rats, rabbits, simians, etc).

"Disorders or diseases" in which altered kinase activity have been implicated specifically include, but are not limited to, human X-linked agammaglobulinemia, nonspherocytic hemolytic anemia, atherosclerosis, carcinomas (breast, ovary, renal, squamous cell and prostate), diabetes, gliomas, glomerular disease, hepatomegaly, Karposi's sarcoma, lymphoblastic and myelogenous leukemias, myoglobinuria, peptic ulcer disease, psoriasis, pulmonary fibrosis, restenosis, and septic shock due to cholera, *Clostridium difficile*, *E. coli* and Shigella.

Since the list of technical and scientific terms cannot be all encompassing, any undefined terms shall be construed to have the same meaning as is commonly understood by one of skill in the art to which this invention belongs. Furthermore, the singular forms "a", "an" and "the" include plural referents unless the context clearly dictates otherwise. For example, reference to a "restriction enzyme" or a "high fidelity enzyme" may include mixtures of such enzymes and any other enzymes fitting the stated criteria, or reference to the method includes reference to one or more methods for obtaining cDNA sequences which will be known to those skilled in the art or will become known to them upon reading this specification.

Before the present sequences, variants, formulations and methods for making and using the invention are described, it is to be understood that the invention is not to be limited only to the particular sequences, variants, formulations or methods described. The sequences, variants, formulations and methodologies may vary, and the terminology used herein is for the purpose of describing particular embodiments. The terminology and definitions are not intended to be limiting since the scope of protection will ultimately depend upon the claims.

DESCRIPTION OF THE INVENTION

The present invention provides for purified partial protein kinase cDNAs which were expressed in various human tissues and isolated therefrom. These sequences were identified by their similarity to published or known open reading frames or untranslated control regions. Since protein kinases are associated with basic cellular processes such as cell proliferation, differentiation and cell signalling, these nucleotide sequences are useful in the characterization of and delineation of normal and abnormal processes. Kinase nucleotide sequences are useful in diagnostic assays used to evaluate the role of a specific kinase in normal, diseased, or therapeutically treated cells.

Purified kinase nucleotide sequences have numerous applications in techniques known to those skilled in the art of molecular biology. These techniques include their use as hybridization probes, for chromosome and gene mapping, in PCR technologies, in the production of sense or antisense nucleic acids, in screening for new therapeutic molecules, etc. These examples are well known and are not intended to be limiting. Furthermore, the nucleotide sequences disclosed herein may be used in molecular biology techniques that have not yet been developed, provided the new techniques rely on properties of nucleotide sequences that are currently known, including but not limited to such properties as the triplet genetic code and specific base pair interactions.

As a result of the degeneracy of the genetic code, a multitude of kinase-encoding nucleotide sequences may be produced and some of these will bear only minimal homology to the endogenous sequence of any known and naturally occurring kinase. This invention has specifically contemplated each and every possible variation of nucleotide sequence that could be made by selecting combinations based on possible codon choices. These combinations are made in accordance with the standard triplet genetic code as applied to the nucleotide sequence of naturally occurring kinases, and all such variations are to be considered as being specifically disclosed.

Although the kinase nucleotide sequences and their derivatives or variants are preferably capable of identifying the nucleotide sequence of the naturally occurring kinase under optimized conditions, it may be advantageous to produce kinase-encoding nucleotide sequences possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding the kinase without altering the encoded amino acid sequence include the production of RNA transcripts having more desirable properties, such as a longer half-life, than transcripts produced from the naturally occurring sequence.

Nucleotide sequences encoding a kinase may be joined to a variety of other nucleotide sequences by means of well established recombinant DNA techniques (Sambrook J. et al (1989) Molecular Cloning: A Laboratory Manual, Cold Spring Harbor Laboratory, Cold Spring Harbor, N.Y.; or Ausubel F. M. et al (1989) Current Protocols in Molecular Biology, John Wiley & Sons, New York City). Useful sequences for joining to the kinase include an assortment of cloning vectors such as plasmids, cosmids, lambda phage derivatives, phagemids, and the like. Vectors of interest include vectors for replication, expression, probe generation, sequencing, and the like. In general, vectors of interest may contain an origin of replication functional in at least one organism, convenient restriction endonuclease sensitive sites, and selectable markers for one or more host cell systems.

PCR as described in U.S. Pat. Nos. 4,683,195; 4,800,195; and 4,965,188 provides additional uses for oligonucleotides based upon the kinase nucleotide sequence. Such oligomers are generally chemically synthesized, but they may be of recombinant origin or a mixture of both. Oligomers generally comprise two nucleotide sequences, one with sense orientation ($5' \rightarrow 3'$) and one with antisense ($3'$ to $5'$) employed under optimized conditions for identification of a specific gene or diagnostic use. The same two oligomers, nested sets of oligomers, or even a degenerate pool of oligomers may be employed under less stringent conditions for identification and/or quantitation of closely related DNA or RNA sequences.

Full length genes may be cloned utilizing partial nucleotide sequence and various methods known in the art. Gobinda et al (1993; PCR Methods Applic 2:318–22) disclose "restriction-site PCR" as a direct method which uses universal primers to retrieve unknown sequence adjacent to a known locus. First, genomic DNA is amplified in the presence of primer to linker and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase. Gobinda et al present data concerning Factor IX for which they identified a conserved stretch of 20 nucleotides in the 3' noncoding region of the gene.

Inverse PCR is the first method to report successful acquisition of unknown sequences starting with primers based on a known region (Triglia T. et al (1988) Nucleic Acids Res 16:8186). The method uses several restriction enzymes to generate a suitable fragment in the known region of a gene. The fragment is then circularized by intramolecular ligation and used as a PCR template. Divergent primers are designed from the known region. The multiple rounds of restriction enzyme digestions and ligations that are necessary prior to PCR make the procedure slow and expensive (Gobinda et al, supra).

Capture PCR (Lagerstrom M. et al (1991) PCR Methods Applic 1:111–19) is a method for PCR amplification of DNA fragments adjacent to a known sequence in human and YAC DNA. As noted by Gobinda et al (supra), capture PCR also requires multiple restriction enzyme digestions and ligations to place an engineered double-stranded sequence into an unknown portion of the DNA molecule before PCR. Although the restriction and ligation reactions are carried out simultaneously, the requirements for extension, immobilization and two rounds of PCR and purification prior to sequencing render the method cumbersome and time consuming.

Parker J. D. et al (1991; Nucleic Acids Res 19:3055–60), teach walking PCR, a method for targeted gene walking which permits retrieval of unknown sequence. PromoterFinder™ is a new kit available from Clontech (Palo Alto, Calif.) which uses PCR and primers derived from p53 to walk in genomic DNA. Nested primers and special PromoterFinder libraries are used to detect upstream sequences such as promoters and regulatory elements. This process avoids the need to screen libraries and is useful in finding intron/exon junctions.

Another new PCR method, "Improved Method for Obtaining Full Length cDNA Sequences" by Guegler et al, patent application Ser. No 08/487,112, filed Jun. 7, 1995 and hereby incorporated by reference, employs XL-PCR (Perkin-Elmer, Foster City, Calif.) to amplify and extend partial nucleotide sequence into longer pieces of DNA. This method was developed to allow a single researcher to process multiple genes (up to 20 or more) at one time and to obtain an extended (possibly full-length) sequence within 6–10 days. This new method replaces methods which use labelled probes to screen plasmid libraries and allow one researcher to process only about 3–5 genes in 14–40 days.

In the first step, which can be performed in about two days, any two of a plurality of primers are designed and synthesized based on a known partial sequence. In step 2, which takes about six to eight hours, the sequence is extended by PCR amplification of a selected library. Steps 3 and 4, which take about one day, are purification of the amplified cDNA and its ligation into an appropriate vector. Step 5, which takes about one day, involves transforming and growing up host bacteria. In step 6, which takes approximately five hours, PCR is used to screen bacterial clones for extended sequence. The final steps, which take about one day, involve the preparation and sequencing of selected clones.

If the full length cDNA has not been obtained, the entire procedure is repeated using either the original library or some other preferred library. The preferred library may be one that has been size-selected to include only larger cDNAs or may consist of single or combined commercially available libraries, eg. lung, liver, heart and brain from Gibco/BRL (Gaithersburg, Md.). The cDNA library may have been prepared with oligo (dT) or random priming. Random primed libraries are preferred in that they will contain more sequences which contain 5' ends of genes. A randomly primed library may be particularly useful if an oligo (dT) library does not yield a complete gene. It must be noted that the larger and more complex the protein, the less likely it is that the complete gene will be found in a single plasmid.

A new method for analyzing either the size or the nucleotide sequence of PCR products is capillary electrophoresis. Systems for rapid sequencing are available from Perkin Elmer (Foster, City Calif.), Beckman Instruments (Fullerton, Calif.), and other companies. Capillary sequencing employs flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. Genotyper™ and Sequence Navigators™ from Perkin Elmer) and the entire process from loading of samples to computer analysis and electronic data display is computer controlled. Capillary electrophoresis provides greater resolution and is many times faster than standard gel based procedures. It is particularly suited to the sequencing of small pieces of DNA which might be present in limited amounts in a particular sample. The reproducible sequencing of up to 350 bp of M13 phage DNA in 30 min has been reported (Ruiz-Martinez M. C. et al (1993) Anal Chem 65:2851–8).

Another aspect of the subject invention is to provide for kinase hybridization probes which are capable of hybridizing with naturally occurring nucleotide sequences encoding kinases. The stringency of the hybridization conditions will determine whether the probe identifies only the native nucleotide sequence of that specific kinase or sequences of closely related molecules. If degenerate kinase nucleotide sequences of the subject invention are used for the detection of related kinase encoding sequences, they should preferably contain at least 50% of the nucleotides of the sequences presented herein. Hybridization probes of the subject invention may be derived from the nucleotide sequences of the SEQ ID NOs 1–44, or from surrounding or included genomic sequences comprising untranslated regions such as promoters, enhancers and introns. Such hybridization probes may be labelled with appropriate reporter molecules. Means for producing specific hybridization probes for kinases include oligolabelling, nick translation, end-labelling or PCR amplification using a labelled nucleotide. Alternatively, the cDNA sequence may be cloned into a vector for the production of mRNA probe. Such vectors are known in the art, are commercially available, and may be used to synthesize RNA probes in vitro by addition of an appropriate RNA polymerase such as T7, T3 or SP6 and labelled nucleotides. A number of companies (such as Pharmacia Biotech, Piscataway, N.J.; Promega, Madison, Wis.; US Biochemical Corp, Cleveland, Ohio; etc.) supply commercial kits and protocols for these procedures.

It is also possible to produce a DNA sequence, or portions thereof, entirely by synthetic chemistry. Sometimes the source of information for producing this sequence comes from the known homologous sequence from closely related organisms. After synthesis, the nucleic acid sequence can be used alone or joined with a preexisting sequence and inserted into one of the many available DNA vectors and their respective host cells using techniques well known in the art. Moreover, synthetic chemistry may be used to introduce specific mutations into the nucleotide sequence. Alternatively, a portion of sequence in which a mutation is desired can be synthesized and recombined with a portion of an existing genomic or recombinant sequence.

The kinase nucleotide sequences can be used individually, or in panels, in a diagnostic test or assay to detect disorder or disease processes associated with abnormal levels of kinase expression. The nucleotide sequence is added to a sample (fluid, cell or tissue) from a patient under hybridizing conditions. After an incubation period, the sample is washed with a compatible fluid which optionally contains a reporter molecule which will bind the specific nucleotide. After the compatible fluid is rinsed off, the reporter molecule is quantitated and compared with a standard for that fluid, cell or tissue. If kinase expression is significantly different from the standard, the assay indicates the presence of disorder or disease. The form of such qualitative or quantitative methods may include northern analysis, dot blot or other membrane based technologies, dip stick, pin or chip technologies, PCR, ELISAs or other multiple sample format technologies.

This same assay, combining a sample with the nucleotide sequence, is applicable in evaluating the efficacy of a particular therapeutic treatment regime. It may be used in animal studies, in clinical trials, or in monitoring the treatment of an individual patient. First, standard expression must be established for use as a basis of comparison. Second, samples from the animals or patients affected by the disorder or disease are combined with the nucleotide sequence to evaluate the deviation from the standard or normal profile. Third, an existing therapeutic agent is administered, and a treatment profile is generated. The assay is evaluated to determine whether the profile progresses toward or returns to the standard pattern. Successive treatment profiles may be used to show the efficacy of treatment over a period of several days or several months.

The nucleotide sequence for any particular kinase (SEQ ID NOs 1–45) can also be used to generate probes for mapping the native genomic sequence. The sequence may be mapped to a particular chromosome or to a specific region of the chromosome using well known techniques. These include in situ hybridization to chromosomal spreads (Verma et al (1988) Human Chromosomes: A Manual of Basic Techniques, Pergamon Press, New York City), flow-sorted chromosomal preparations, or artificial chromosome constructions such as yeast artificial chromosomes (YACs), bacterial artificial chromosomes (BACs), bacterial P1 constructions or single chromosome cDNA libraries.

In situ hybridization of chromosomal preparations and physical mapping techniques such as linkage analysis using established chromosomal markers are invaluable in extending genetic maps. Examples of genetic maps can be found in the 1994 Genome Issue of Science (265:1981f). Often the placement of a gene on the chromosome of another mammalian species may reveal associated markers even if the number or arm of a particular human chromosome is not known. New partial nucleotide sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22-23 (Gatti et al (1988) Nature 336:577–580), any sequences mapping to that area may represent genes for further investigation. The nucleotide sequences of the subject invention may also be used to detect differences in the chromosomal location of nucleotide sequences due to translocation, inversion, etc. between normal and carrier or affected individuals.

The partial nucleotide sequence encoding a particular kinase may be used to produce an amino acid sequence using well known methods of recombinant DNA technology. Goeddel (1990, Gene Expression Technology, Methods and Enzymology, Vol 185, Academic Press, San Diego, Calif.) is one among many publications which teach expression of an isolated, purified nucleotide sequence. The amino acid or peptide may be expressed in a variety of host cells, either prokaryotic or eukaryotic. Host cells may be from the same species from which the nucleotide sequence was derived or from a different species. Advantages of producing an amino acid sequence or peptide by recombinant DNA technology include obtaining adequate amounts for purification and the availability of simplified purification procedures.

Cells transformed with a kinase nucleotide sequence may be cultured under conditions suitable for the expression and recovery of peptide from cell culture. The peptide produced by a recombinant cell may be secreted or may be contained intracellularly depending on the sequence itself and/or the vector used. In general, it is more convenient to prepare recombinant proteins in secreted form, and this is accomplished by ligating kin to a recombinant nucleotide sequence which directs its movement through a particular prokaryotic or eukaryotic cell membrane. Other recombinant constructions may join kin to nucleotide sequence encoding a polypeptide domain which will facilitate protein purification (Kroll D. J. et al (1993) DNA Cell Biol 12:441–53).

Direct peptide synthesis using solid-phase techniques (Stewart et al (1969) Solid-Phase Peptide Synthesis, WH Freeman Co, San Francisco, Calif.; Merrifield J. (1963) J Am Chem Soc 85:2149–2154) is an alternative to recombinant or chimeric peptide production. Automated synthesis may be achieved, for example, using Applied Biosystems 431A Peptide Synthesizer in accordance with the instructions provided by the manufacturer. Additionally a particular kinase sequence or any part thereof may be mutated during direct synthesis and combined using chemical methods with other kinase sequence(s) or a part thereof. This chimeric nucleotide sequence can also be placed in an appropriate vector and host cell to produce a variant peptide.

Although an amino acid sequence or oligopeptide used for antibody induction does not require biological activity, it must be immunogenic. KIN used to induce specific antibodies may have an amino acid sequence consisting of at least five amino acids and preferably at least 10 amino acids. Short stretches of amino acid sequence may be fused with those of another protein such as keyhole limpet hemocyanin, and the chimeric peptide used for antibody production. Alternatively, the oligopeptide may be of sufficient length to contain an entire domain.

Antibodies specific for KIN may be produced by inoculation of an appropriate animal with an antigenic fragment of the peptide. An antibody is specific for KIN if it is produced against an epitope of the polypeptide and binds to at least part of the natural or recombinant protein. Antibody production includes not only the stimulation of an immune response by injection into animals, but also analogous processes such as the production of synthetic antibodies, the screening of recombinant immunoglobulin libraries for specific-binding molecules (Orlandi R. et al (1989) PNAS 86:3833–3837, or Huse W. D. et al (1989) Science 256:1275–1281), or the in vitro stimulation of lymphocyte populations. Current technology (Winter G. and Milstein C. (1991) Nature 349:293–299) provides for a number of highly specific binding reagents based on the principles of antibody formation. These techniques may be adapted to produce molecules which specifically bind kinase peptides. Antibodies or other appropriate molecules generated against a specific immunogenic peptide fragment or oligopeptide can be used in Western analysis, enzyme-linked immunosorbent assays (ELISA) or similar tests to establish the presence of or to quantitate amounts of kinase active in normal, diseased, or therapeutically treated cells or tissues.

The examples below are provided to illustrate the subject invention. These examples are provided by way of illustration and are not included for the purpose of limiting the invention.

EXAMPLES

I cDNA Library Construction

The kinase sequences of this application (Table 1) were first identified among the sequences comprising various libraries. Technology has advanced considerably since the first cDNA libraries were made. Many small variations in both chemicals and machinery have been instituted over time, and these have improved both the efficiency and safety of the process. Although the cDNAs could be obtained using an older procedure, the procedure presented in this application is exemplary of one currently being used by persons skilled in the art. For the purpose of providing an exemplary method, the tissue preparation, mRNA isolation and cDNA library construction described here is for the rheumatoid synovium library from which the Incyte Clones 191283 and 192268 for ser/thr kinases were obtained.

Rheumatoid synovial tissue was obtained from the hip joint removed from a 68 year old female with erosive, nodular rheumatoid arthritis. The tissue was frozen, ground to powder in a mortar and pestle, and lysed immediately in buffer containing guanidinium isothiocyanate. The lysate was centrifuged over a CsCl cushion (18 hrs at 25,000 rpm using a Beckman SW28 rotor and ultracentrifuge; Beckman Instruments, Palo Alto, Calif.), ethanol precipitated, resuspended in water and DNase treated for 15 min at 37° C. The RNA was extracted with phenol chloroform and precipitated with ethanol. Polyadenylated messages were isolated using Qiagen Oligotex (QIAGEN Inc, Chatsworth, Calif.), and a custom cDNA library was constructed by Stratagene (La Jolla, Calif.).

First strand cDNA synthesis was accomplished using an oligo (dT) primer/linker which also contained an XhoI restriction site. Second strand synthesis was performed using a combination of DNA polymerase I, *E. coli* ligase and RNase H, followed by the addition of an EcoRI linker to the blunt ended cDNA. The EcoRI linked, double-stranded cDNA was then digested with XhoI restriction enzyme, extracted with phenol chloroform, and fractionated by size on Sephacryl S400. DNA of the appropriate size was then ligated to dephosphorylated Lambda Zap® arms (Stratagene) and packaged using Gigapack extracts (Stratagene). pBluescript (Stratagene) phagemid DNAs were excised en masse from the library.

In the alternative, DNAs were purified using Miniprep Kits (Catalog #77468; Advanced Genetic Technologies Corporation, Gaithersburg, Md.). These kits provide a 96-well format and enough reagents for 960 purifications. The recommended protocol supplied with each kit has been employed except for the following changes. First, the 96 wells are each filled with only 1 ml of sterile Terrific broth (LIFE TECHNOLGIES™, Gaithersburg, Md.) with carbenicillin at 25 mg/L (2xCarb) and glycerol at 0.4%. After the wells are inoculated, the bacteria are cultured for 24 hours and lysed with 60 μl of lysis buffer. A centrifugation step (2900 rpm for 5 minutes) is performed before the contents of the block are added to the primary filter plate. The optional step of adding isopropanol to TRIS buffer is not routinely performed. After the last step in the protocol, samples are transferred to a Beckman 96-well block for storage.

II Sequencing of cDNA Clones

The cDNA inserts from random isolates of the rheumatoid synovium or other appropriate library were sequenced in part. Methods for DNA sequencing are well known in the art and employ such enzymes as the Klenow fragment of DNA polymerase I, SEQUENASE® (US Biochemical Corp) or Taq polymerase. Methods to extend the DNA from an oligonucleotide primer annealed to the DNA template of interest have been developed for both single- and double-stranded templates. Chain termination reaction products were separated using electrophoresis and detected via their incorporated, labelled precursors. Recent improvements in mechanized reaction preparation, sequencing and analysis have permitted expansion in the number of sequences that can be determined per day. Preferably, the process is automated with machines such as the Hamilton Micro Lab 2200

(Hamilton, Reno, Nev.), Peltier Thermal Cycler (PTC200; MJ Research, Watertown Mass.) and the Applied Biosystems Catalyst 800 and 377 and 373 DNA sequencers.

The quality of any particular cDNA library may be determined by performing a pilot scale analysis of 192 cDNAs and checking for percentages of clones containing vector, lambda or *E. coli* DNA, mitochondrial or repetitive DNA, and clones with exact or homologous matches to public databases. The number of unique sequences—those having no known match in any available database—were recorded.

III Homology Searching of cDNA Clones and Their Deduced Proteins

Each sequence so obtained was compared to sequences in GenBank using a search algorithm developed by Applied Biosystems and incorporated into the INHERIT™ 670 Sequence Analysis System. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

Alternatively, BLAST, which stands for Basic Local Alignment Search Tool, is used to search for local sequence alignments (Altschul S. F. (1993) J Mol Evol 36:290–300; Altschul, S. F. et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. While it is useful for matches which do not contain gaps, it is inappropriate for performing motif-style searching. The fundamental unit of BLAST algorithm output is the High-scoring Segment Pair (HSP).

An HSP consists of two sequence fragments of arbitrary but equal lengths whose alignment is locally maximal and for which the alignmentBLAST approach is to look threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

All the kinase molecules presented in this application were examined using INHERIT. Although their identification was based on the criteria above, their homology to known kinase molecules and name are subject to change when additional computer analysis against additional or more recent database information is employed. For example, whereas the first two kinases in Table 1 were initially identified as unique Incyte clones, homologous mouse and human kinases are now known. In other cases, additional sequence information has become available and its review against the known databases has precipitated a name change. Occasionally a clone number will also disappear from the LIFESEQ™ database (Incyte Pharmaceuticals Inc, Palo Alto, Calif.). This situation generally arises during the regular review of clones and assembly of contiguous sequences.

IV Extension of cDNAs to Full Length

The kinase sequences presented here can be used to design oligonucleotide primers for the extension of the cDNAs to full length. In fact, the partial map kinase cDNA sequence (SEQ ID NO 38) initially identified in Incyte clone 214915 among the sequences comprising the human stomach cell library was extended to full length as shown in "A Novel Human Map Kinase Homolog" by Hawkins et al. Incyte Docket PF-036P, filed on Jun. 28, 1995, incorporated herein by reference. The coding region of this full length sequence (SEQ ID NO 45; Incyte Clone 214915E) begins at nucleotide 58 and ends at nucleotide 1156.

Primers are designed based on known sequence; one primer is synthesized to initiate extension in the antisense direction (XLR) and the other to extend sequence in the sense direction (XLF). The primers allow the sequence to be extended "outward" generating amplicons containing new, unknown nucleotide sequence for the gene of interest. The primers may be designed using Oligo 4.0 (National Biosciences Inc, Plymouth, Minn.), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations was avoided.

The stomach cDNA library was used as a template, and XLR=AAG ACA TCC AGG AGC CCA ATG AC and XLF=AGG TGA TCC TCA GCT GGA TGC AC primers were used to extend and amplify the 214915 sequence. By following the instructions for the XL-PCR kit and thoroughly mixing the enzyme and reaction mix, high fidelity amplification is obtained. Beginning with 25 pMol of each primer and the recommended concentrations of all other components of the kit, PCR is performed using the Peltier Thermal Cycler (PTC200; MJ Research, Watertown, Mass.) and the following parameters:

Step 1 94° C. for 60 sec (initial denaturation)
Step 2 94° C. for 15 sec
Step 3 65° C. for 1 min
Step 4 68° C. for 7 min
Step 5 Repeat step 2–4 for 15 additional cycles
Step 6 94° C. for 15 sec
Step 7 65° C. for 1 min
Step 8 68° C. for 7 min+15 sec/cycle
Step 9 Repeat step 6–8 for 11 additional cycles
Step 10 72° C. for 8 min
Step 11 4° C. (and holding)

At the end of 28 cycles, 50 µl of the reaction mix was removed; and the remaining reaction mix was run for an additional 10 cycles as outlined below:

Step 1 94° C. for 15 sec
Step 2 65° C. for 1 min

Step 3 68° C. for (10 min+15 sec)/cycle

Step 4 Repeat step 1–3 for 9 additional cycles

Step 5 72° C. for 10 min

A 5–10 µl aliquot of the reaction mixture is analyzed by electrophoresis on a low concentration (about 0.6–0.8%) agarose mini-gel to determine which reactions were successful in extending the sequence. Although all extensions potentially contain a full length gene, some of the largest products or bands are selected and cut out of the gel. Further purification involves using a commercial gel extraction method such as QIAQuick™ (QIAGEN Inc). After recovery of the DNA, Klenow enzyme is used to trim single-stranded, nucleotide overhangs creating blunt ends which facilitate religation and cloning.

After ethanol precipitation, the products are redissolved in 13 µl of ligation buffer. Then, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook J. et al, supra). After incubation for one hour at 37° C., the whole transformation mixture is plated on Luria Bertani (LB)-agar (Sambrook J. et al, supra) containing 2×Carb. The following day, 12 colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 15 µl of concentrated PCR reaction mix (1.33×) containing 0.75 units of Taq polymerase, a vector primer and one or both of the gene specific primers used for the extension reaction are added to each well. Amplification is performed using the following conditions:

Step 1 94° C. for 60 sec

Step 2 94° C. for 20 sec

Step 3 55° C. for 30 sec

Step 4 72° C. for 90 sec

Step 5 Repeat steps 2–4 for an additional 29 cycles

Step 6 72° C. for 180 sec

Step 7 4° C. (and holding)

Aliquots of the PCR reactions are run on agarose gels together with molecular weight markers. The sizes of the PCR products are compared to the original partial cDNAs, and appropriate clones are selected, ligated into plasmid and sequenced.

V Diagnostic Assays Using Kinase Specific Oligomers

In those cases where a specific disorder or disease (see definitions supra) is suspected to involve altered quantities of a particular kinase, oligomers may be designed to establish the presence and/or quantity of mRNA expressed in a biological sample. There are several methods currently being used to quantitate the expression of a particular molecule. Most of these methods use radiolabelled (Melby P. C. et al 1993 J Immunol Methods 159:235–44) or biotinylated (Duplaa C. et al 1993 Anal Biochem 229–36) nucleotides, coamplification of a control nucleic acid, and standard curves onto which the experimental results are interpolated. For example, phosphorylase B kinase deficiency may manifest as hepatomegaly which is inherited as either an X-linked or autosomal recessive trait or myoglobinuria whose inheritance is unknown.

Oligomers for phosphorylase B kinase are first used in quantitative PCR to establish a normal range for expression of phosphorylase B kinase. Then, these same oligomers are used with extracts of cells from patients with inherited phosphorylase B kinase deficiency. The information from such studies is used to define different inheritance patterns and to diagnose future patients displaying phosphorylase B kinase deficiency-like symptoms. In like manner, this same assay can be used to monitor progress of the patient as his/her physiological situation moves toward the normal range during therapy for the condition.

VI Kinases Kit

The kinases of the subject invention are used to produce a kinases kit for diagnosing disorders or diseases associated with altered kinase expression. This involves the designing a plurality of oligomers, one set of which is specific for each kinase or kinase regulatory sequence. Specificity in this case refers to sequence similarity, to the length of the nucleic acid molecule amplified, to cell or tissue type being screened or to the disorder or disease. These oligomers are combined with a biological sample obtained from a patient in a solution sufficient for PCR and amplified. The PCR products are examined first, to detect the expression of each kinase, and second to quantify the expression of each kinase. Kinase expression is compared with standard ranges for normal and abnormal expression. In the case(s) where kinase expression is altered, use of the kit has provided the physician with a named disorder or disease which can be treated or further investigated.

A further use of the oligomers from the kinases kit is in a diagnostic assay of example V (above) used to monitor patient response to drug therapy. Once the disease has been named and a therapy chosen, the oligomers specific to the patient's disease may be used periodically to monitor the efficacy of the chosen therapy. In this case, the specific oligomers are combined with a biological sample from the patient in a solution sufficient for PCR and amplified. The PCR product is quantified and compared with a normal standard and with the pretreatment profile of the patient. If the kinase expression is tending toward normal, the therapy may be considered effective; if the expression is even more abnormal, therapy should be discontinued and an alternative treatment instituted.

VII Sense or Antisense Molecules

Knowledge of the correct cDNA sequence of any particular kinase, its regulatory elements or parts thereof will enable its use as a tool in sense (Youssoufian H. and H. F. Lodish 1993) Mol Cell Biol 13:98–104) or antisense (Eguchi et al (1991) Annu Rev Biochem 60:631–652) technologies for the investigation of gene function. Oligonucleotides, from genomic or cDNAs, comprising either the sense or the antisense strand of the cDNA sequence can be used in vitro or in vivo to inhibit expression. Such technology is now well known in the art, and oligonucleotides or other fragments can be designed from various locations along the sequences.

The gene of interest can be turned off in the short term by transfecting a cell or tissue with expression vectors which will flood the cell with sense or antisense sequences until all copies of the vector are disabled by endogenous nucleases. Stable transfection of appropriate germ line cells or preferably a zygote with a vector containing the fragment will produce a transgenic organism (U.S. Pat. No. 4,736,866, 12 Apr. 1988), which produces enough copies of the sense or antisense sequence to significantly compromise or entirely eliminate normal activity of the particular kinase gene. Frequently, the function of the gene can be ascertained by observing behaviors such as lethality, loss of a physiological pathway, changes in morphology, etc. at the intracellular, cellular, tissue or organismal level.

In addition to using fragments constructed to interrupt transcription of the open reading frame, modifications of gene expression can be obtained by designing antisense sequences to promoters, enhancers, introns, or even to trans-acting regulatory genes. Similarly, inhibition can be achieved using Hogeboom base-pairing methodology, also known as "triple helix" base pairing.

VIII Expression of Kinases

Expression of the kinases may be accomplished by subcloning the cDNAs into appropriate vectors and transfecting the vectors into host cells. In some cases, the cloning vector previously used for the generation of the tissue library also provides for direct expression of kinase sequences in *E. coli*. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods will produce a fusion protein corresponding to the first seven residues of β-galactosidase, about 5 to 15 residues which correspond to linker, and the peptide encoded within the kinase cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion.

The kinase cDNA can be shuttled into other vectors known to be useful for expression of protein in specific hosts. Oligonucleotide linkers containing cloning sites as well as a stretch of DNA sufficient to hybridize to the end of the target cDNA (25 bases) can be synthesized chemically by standard methods. These primers can then used to amplify the desired gene fragments by PCR. The resulting fragments can be digested with appropriate restriction enzymes under standard conditions and isolated by gel electrophoresis. Alternatively, similar gene fragments can be produced by digestion of the cDNA with appropriate restriction enzymes and filling in the missing gene sequence with chemically synthesized oligonucleotides. Partial nucleotide sequence from more than one gene can be ligated together and cloned in appropriate vectors to optimize expression.

Suitable expression hosts for such chimeric molecules include but are not limited to mammalian cells such as Chinese Hamster Ovary (CHO) and human 293 cells, insect cells such as Sf9 cells, yeast cells such as *Saccharomyces cerevisiae*, and bacteria such as *E. coli*. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, some of the kinase vectors may contain native promoters which will allow induction of gene expression in human cells such as the 293 line mentioned above. Other available promoters are host specific and may be specifically combined with the coding region of the kinase of interest. They include MMTV, SV40, and metallothionine promoters for CHO cells; trp, lac, tac and T7 promoters for bacterial hosts; and alpha factor, alcohol oxidase and PGH promoters for yeast. In addition, transcription enhancers, such as the rous sarcoma virus (RSV) enhancer, may be used in mammalian host cells. Once homogeneous cultures of recombinant cells are obtained through standard culture methods, large quantities of recombinantly produced peptide can be recovered from the conditioned medium and analyzed using methods known in the art.

IX Isolation of Recombinant KIN

KIN may be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a cleavable linker sequence such as Factor XA or enterokinase (Invitrogen) between the purification domain and the kin sequence may be useful to facilitate expression of KIN.

X Testing for Kinase Activity

The sequences in this application represent many different domains of different kinase families. These domains (and subdomains as detailed in the background of the invention) may be utilized: 1) individually for the production of antibodies, 2) in functional groups (eg. to span a membrane), and 3) as interchangable, usable parts of a chimeric kinase. The various partial cDNA sequences of this application represent the different kinase domains of the various families (Hardie G. and Hanks S., supra), and they may be recombined in numerous ways to produce chimeric nucleic acid molecules. For example, a known, full length kinase such as the human map kinase of this application (Seq ID No 45) may be used to swap related portions of the nucleic acid sequence, analogous to domains or subdomains of MAP kinase polypeptides. The chimeric nucleotides, so produced, may be introduced into prokaryotic host cells (as reviewed in Strosberg A. D. and Marullo S. (1992) Trends Pharma Sci 13:95–98) or eukaryotic host cells. These host cells are then employed in procedures to determine what molecules activate the kinase or what molecules are activated by a kinase. Such activating or activated molecules may be of extracellular, intracellular, biologic or chemical origin.

An example of a test system, in this case for protein tyrosine kinases, can be based on the interaction of protein tyrosine kinases with chemokine receptors (Taniguchi T. (1995) Science 268:251–255). These receptors are capable of activating a variety of nonreceptor protein tyrosine kinases when stimulated by an extracellular chemokine. C-X-C chemokines such as platelet factor 4, interleukin-8, connective tissue activating protein III, neutrophil activating peptide 2, are soluble activators of neutrophils.

A standard measure of neutrophil activation involves measuring the mobilization of $Ca^{++}$ as part of the signal transduction pathway. The experiment involves several steps. First, blood cells obtained from venipuncture are fractionated by centrifugation on density gradients. Enriched populations of neutrophils are further fractionated on columns by negative selection using antibodies specific for other blood cells types. Next, neutrophils are transformed with an expression vector containing the kinase nucleic acid sequence of interest and preloaded fluorescent probe whose emission characteristics have been altered by $Ca^{++}$ binding. Or in the alternative, the neutrophil is preloaded with the purified kinase of interest and fluorescent probe. Then, when the cells are exposed to an appropriate chemokine, the chemokine receptor activates the kinase which, in turn, initiates $Ca^{++}$ flux. $Ca^{++}$ mobilization is observed and measured using fluorometry as has been described in Grynkievicz G. et al (1985) J Biol Chem 260:3440, and McColl S. et al (1993) J Immunol 150:4550–4555, incorporated herein by reference.

XI Identification of or Production of Kinase Specific Antibodies

Purified KIN is used to screen a pre-existing antibody library or to raise antibodies. using either polyclonal or monoclonal methodology. For polyclonal antibody production, denatured peptide from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. In identifying mouse hybridomas, the denatured protein can be labelled and used to screen potential murine B-cell hybridomas for those which produce antibody. This procedure requires only small quantities of protein, such that 20 mg would be sufficient for labelling and screening of several thousand clones.

For monoclonal antibody production, the amino acid sequence, as deduced from translation of the cDNA, is analyzed to determine regions of high immunogenicity. Peptides comprising appropriate hydrophilic regions are expressed from recombinant cDNA or synthesized and used in suitable immunization protocols to raise antibodies. Selection of appropriate epitopes is described by Ausubel F. M. et al (supra). The optimal amino acid sequences for immunization are usually located at the C-terminus or N-terminus and in intervening, hydrophilic regions of the polypeptide which are likely to be exposed to the external environment when the protein is in its natural conformation.

Typically, selected oligopeptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl-N-hydroxysuccinimide ester (MBS; Ausubel F. M. et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% bovine serum albumin, reacting with antisera, washing and reacting with labelled, affinity purified, specific goat anti-rabbit IgG.

Hybridomas may also be prepared and screened using standard techniques. Hybridomas of interest are detected by screening with labelled KIN to identify those fusions producing the monoclonal antibody with the desired specificity. In a typical protocol, wells of plates (FAST; Becton-Dickinson, Palo Alto, Calif.) are coated during incubation with affinity purified, specific rabbit anti-mouse (or suitable anti-species Ig) antibodies at 10 mg/ml. The coated wells are blocked with 1% BSA, washed and incubated with supernatants from hybridomas. After washing the wells are incubated with labelled KIN at 1 mg/ml. Supernatants with specific antibodies bind more labelled KIN than is detectable in the background. Then clones producing specific antibodies are expanded and subjected to two cycles of cloning at limiting dilution. Cloned hybridomas are injected into pristane-treated mice to produce ascites, and monoclonal antibody is purified from mouse ascitic fluid by affinity chromatography on Protein A. Monoclonal antibodies with affinities of at least $10^8$/M, preferably $10^9$ to $10^{10}$ or stronger, will typically be made by standard procedures as described in Harlow and Lane (1988) Antibodies: A Laboratory Manual, Cold Spring Harbor Laboratory, Cold Spring Harbor, N.Y.; and in Goding (1986) Monoclonal Antibodies: Principles and Practice, Academic Press, New York City, both incorporated herein by reference.

XII Diagnostic Assays Using KIN Specific Antibodies

Particular KIN antibodies are useful for investigation of various disorders or diseases which may be characterized by differences in the amount or distribution of KIN. Given the usual role of the kinases, KIN might be expected to be upregulated (or downregulated) in its involvement in activation of signal cascades.

Diagnostic assays for KIN include methods utilizing the antibody and a reporter molecule to detect KIN in human body fluids, membranes, cells, tissues or extracts thereof. The antibodies of the present invention may be used with or without modification. Frequently, the antibodies will be labelled by joining them, either covalently or noncovalently, with a substance which provides for a detectable signal. A wide variety of reporter molecules and conjugation techniques are known and have been reported extensively in both the scientific and patent literature. Suitable reporter molecules or labels include those radionuclides, enzymes, fluorescent, chemi-luminescent, or chromogenic agents previously mentioned as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immuno-globulins may be produced as shown in U.S. Pat. No. 4,816,567, incorporated herein by reference.

A variety of protocols for measuring soluble or membrane-bound KIN, using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on KIN is preferred, but a competitive binding assay may be employed. These assays are described, among other places, in Maddox, D. E. et al (1983, J Exp Med 158:1211).

XIII Purification of Native KIN Using Antibodies

Native or recombinant protein kinases can be purified by immunoaffinity chromatography using antibodies specific for that particular KIN. In general, an immunoaffinity column is constructed by covalently coupling the anti-KIN antibody to an activated chromatographic resin.

Polyclonal immunoglobulins are prepared from immune sera either by precipitation with ammonium sulfate or by purification on immobilized Protein A (Pharmacia Biotech). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia Biotech). The antibody is coupled to the resin, the resin is blocked, and the derivative resin is washed according to the manufacturer's instructions.

Such immunoaffinity columns may be utilized in the purification of KIN by preparing a fraction from cells containing KIN in a soluble form. This preparation may be derived by solubilization of whole cells or of a subcellular fraction obtained via differential centrifugation (with or without addition of detergent) or by other methods well known in the art. Alternatively, soluble KIN containing a signal sequence may be secreted in useful quantity into the medium in which the cells are grown.

A soluble KIN-containing preparation is passed over the immunoaffinity column, and the column is washed under conditions that allow the preferential absorbance of KIN (eg, high ionic strength buffers in the presence of detergent). Then, the column is eluted under conditions that disrupt antibody/KIN binding (eg, a buffer of pH 2–3 or a high concentration of a chaotrope such as urea or thiocyanate ion), and KIN is collected.

XIV Drug Screening

This invention is particularly useful for screening therapeutic compounds by using binding fragments of KIN in any of a variety of drug screening techniques. The molecules to be screened may be of extracellular, intracellular, biologic or chemical origin. The peptide fragment employed in such a test may either be free in solution, affixed to a solid support, borne on a cell surface or located intracellularly. One may measure, for example, the formation of complexes between KIN and the agent being tested. Alternatively, one can examine the diminution in complex formation between KIN and a receptor caused by the agent being tested.

Methods of screening for drugs or any other agents which can affect signal transduction comprise contacting such an agent with KIN fragment and assaying for the presence of a complex between the agent and the KIN fragment. In such assays, the KIN fragment is typically labelled. After suitable incubation, free KIN fragment is separated from that present in bound form, and the amount of free or uncomplexed label is a measure of the ability of the particular agent to bind to KIN.

Another technique for drug screening provides high throughput screening for compounds having suitable binding affinity to the KIN polypeptides and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with KIN fragment and washed. Bound KIN fragment is then detected by methods well known in the art. Purified KIN can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding KIN specifically compete with a test compound for binding to KIN fragments. In this manner, the antibodies can be used to detect the presence of any peptide which shares one or more antigenic determinants with KIN.

XV Identification of Molecules Which Interact with KIN

The inventive purified KIN is a research tool for identification, characterization and purification of interacting, signal transduction pathway proteins. Appropriate labels are incorporated into KIN by various methods known in the art and KIN is used to capture soluble or interact with membrane-bound molecules. A preferred method involves labeling the primary amino groups in KIN with $^{125}$I Bolton-Hunter reagent (Bolton, A. E. and Hunter, W. M. (1973) Biochem J 133:529). This reagent has been used to label various molecules without concomitant loss of biological activity (Hebert C. A. et al (1991) J Biol Chem 266:18989–94; McColl S. et al (1993) J Immunol 150:4550–4555). Membrane-bound molecules are incubated with the labelled KIN molecules, washed to removed unbound molecules, and the KIN complex is quantified. Data obtained using different concentrations of KIN are used to calculate values for the number, affinity, and association of KIN with the signal transduction complex.

Labelled KIN fragments are also useful as a reagent for the purification of molecules with which KIN interacts, specifically including inhibitors. In one embodiment of affinity purification, KIN is covalently coupled to a chromatography column. Cells and their membranes are extracted, KIN is removed and various KIN-free subcomponents are passed over the column. Molecules bind to the column by virtue of their KIN affinity. The KIN-complex is recovered from the column, dissociated and the recovered molecule is subjected to N-terminal protein sequencing. This amino acid sequence is then used to identify the captured molecule or to design degenerate oligomers for cloning its gene from an appropriate cDNA library.

In an alternate method, monoclonal antibodies raised against KIN fragments are screened to identify those which inhibit the binding of labelled KIN. These monoclonal antibodies are then used in affinity purification or expression cloning of associated molecules. Other soluble binding molecules are identified in a similar manner. Labelled KIN is incubated with extracts or other appropriate materials derived from rheumatoid synovium. After incubation, KIN complexes (which are larger than the lone KIN fragment) are identified by a sizing technique such as size exclusion chromatography or density gradient centrifugation and are purified by methods known in the art. The soluble binding protein(s) are subjected to N-terminal sequencing to obtain information sufficient for database identification, if the soluble protein is known, or for cloning, if the soluble protein is unknown.

XVI Use and Administration of Antibodies or Other Inhibitory Molecules

Antibodies, inhibitors, receptors or antagonists of KIN fragments (or other treatments to limit signal transduction, TST), can provide different effects when administered therapeutically. TSTs will be formulated in a nontoxic, inert, pharmaceutically acceptable aqueous carrier medium preferably at a pH of about 5 to 8, more preferably 6 to 8, although the pH may vary according to the characteristics of the antibody, inhibitor, or antagonist being formulated and the condition to be treated. Characteristics of TSTs include solubility of the molecule, half-life and antigenicity/immunogenicity; these and other characteristics may aid in defining an effective carrier. Native human proteins are preferred as TSTs, but organic or synthetic molecules resulting from drug screens may be equally effective in particular situations.

TSTs may be delivered by known routes of administration including but not limited to topical creams and gels; transmucosal spray and aerosol; transdermal patch and bandage; injectable, intravenous and lavage formulations; and orally administered liquids and pills particularly formulated to resist stomach acid and enzymes. The particular formulation, exact dosage, and route of administration will be determined by the attending physician and will vary according to each specific situation.

Such determinations are made by considering multiple variables such as the condition to be treated, the TST to be administered, and the pharmacokinetic profile of the particular TST. Additional factors which may be taken into account include disease state (e.g. severity) of the patient, age, weight, gender, diet, time and frequency of administration, drug combination, reaction sensitivities, and tolerance/response to therapy. Long acting TST formulations might be administered every 3 to 4 days, every week, or once every two weeks depending on half-life and clearance rate of the particular TST.

Normal dosage amounts may vary from 0.1 to 100,000 micrograms, up to a total dose of about 1 g, depending upon the route of administration. Guidance as to particular dosages and methods of delivery is provided in the literature. See U.S. Pat. No. 4,657,760; 5,206,344; or 5,225,212. Those skilled in the art will employ different formulations for different TSTs. Administration to cells such as nerve cells necessitates delivery in a manner different from that to other cells such as vascular endothelial cells.

It is contemplated that disorders or diseases which trigger defensive signal transduction may precipitate damage that is treatable with TSTs. These disorders or diseases may be specifically diagnosed by the tests discussed above, and such testing should be performed in cases where physiologic or pathologic problems are suspected to be associated with abnormal signal transduction.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

TABLE 1

| Clone | Library | GenBank/SwissProt Identifier, Name |
|---|---|---|
| 297 | U937 | P00540 Mouse protooncogene ser/thr kinase |
| 1622 | U937 | HUMCLK3B clk3 gene product |
| 10007 | THP-1 Phorbol LPS | HSPLK1 protein kinase |
| 12702 | THP-1 Phorbol LPS | RATSGPK ser/thr kinase |
| 23789 | Inflamed Adenoid | CHKFRNK chicken tyr kinase |
| 35652 | HUVEC | KEK5 Chicken Y kinase receptor |
| 35855 | HUVEC | HUMANBTK37 tyr kinase |
| 40194 | T + B Lymphoblast | KRB1 VARV Variola virus protein kinase |
| 42170 | T + B Lymphoblast | HSU09564 serine kinase |
| 46081 | Corneal Stroma | YSCKIN1 yeast protein kinase |
| 46651 | Corneal Stroma | CDK4, P11802 |
| 53840 | Fibroblast | HSDAPK, Death-associated protein kinase |
| 54065 | Fibroblast | SCPROKIN 1 yeast 35.6 kD |
| 56494 | Fibroblast | KLMC RAT, myosin light chain kinase |
| 58029 | Skeletal Muscle | ATHCTRIA 1 *A. Thaliana* Y kinase receptor |
| 64663 | Placenta | KIN3 Yeast protein kinase P22209 |
| 67967 | HUVEC Sheer Stress | YAK1 Yeast protein kinase |
| 68963 | HUVEC Sheer Stress | KATK Human Y kinase |
| 71904 | Placenta | KIN3 P22209SwP |
| 75289 | THP-1 Phorbol | H5U08023 Avian retrovirus rp130 |
| 81865 | Rheumatoid Synovium | SNF1 Yeast C catabolite derepressing |
| 82056 | HUVEC Sheer Stress | P34314 *C. elegans* ser/thr kinase |
| 108485 | AML Blast | KAPA Pig cAMP-dependent protein kinase |
| 114973 | Testis | CC2B ARATH Mouse-ear cress cdc |
| 118591 | Skeletal Muscle | PBO192 mixed lineage kinase 1 |
| 119819 | Skeletal Muscle | H5U09564 ser kinase |
| 120376 | Skeletal Muscle | U01064 Y kinase |
| 132750 | Bone Marrow | MLK2 mixed lineage kinase 2 |
| 140052 | T Lymphocyte | G-protein coupled receptor kinase |
| 146392 | T Lymphocyte | SCYAK1 Yeast Yak1 kinase |
| 156108 | THP-1 Phorbol LPS | U01064 Dictyostelium Y kinase |
| 173627 | Bone Marrow | MMU14166 Kiz |
| 181971 | Placenta | HUMTKR Y kinase receptor |
| 182538 | Placenta | HSNEK2R kinase |
| 184416* | Cardiac Muscle | KPKS Human proto-oncogene Ser/Thr kinase |
| 191283 | Rheumatoid Synovium | RATSGPK Ser/Thr kinase |
| 192268 | Rheumatoid Synovium | ATHAPK1A Ser/Thr kinase |
| 214915 | Stomach | XLMPK2K Map kinase |
| 223163 | Pancreas | TGF-β receptor ser/thr kinase |
| 237002 | Small Intestine | P16227 Mouse Y kinase blk |
| 239990 | Hippocampus | SHC Human transforming protein |
| 240142 | Hippocampus | HSNEK2R |
| 275781 | Testes | BOVCKIA casein kinase |
| 285465 | Eosinophils | DDIMLCK myosin light chain kinase |

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
( A ) LENGTH: 526 base pairs (B) TYPE: nucleic acid
(C) STRANDEDNESS: single
(D) TOPOLOGY: linear (ii) MOLECULE TYPE: cDNA (vii) IMMEDIATE SOURCE:
(A) LIBRARY: U937
(B) CLONE: 297

(xi) SEQUENCE DESCRIPTION: SEQ ID NO:1:

| | | | | | | |
|---|---|---|---|---|---|---|
| ACAAGGGTTG | TAATTAAAGG | CGATTTTGAA | ACAATTAAAA | TCTGTGATGT | AGGAGTCTCT | 60 |
| CTACCACTGG | ATGAAAATAT | GACTGTGACT | GACCCTGAGG | CTTGTTACAT | TGGCACAGAG | 120 |
| CCATGGAAAC | CCAAAGAAGC | TGTGGAGGAG | AATGGTGTTA | TTACTGCAAG | GCAGACATAT | 180 |
| TTGCCTTTGG | CTTACTTTGT | GGGAAATGAT | GACTTTATCG | ATTCCACACA | TTAATCTTTC | 240 |
| AAATGATGAT | GATGATGAAG | TAAAAACTTT | TTGATGAAAA | GTAATTTTGA | TGTTGAAGCA | 300 |
| TTACTATGCA | AGCCCTTTGG | ACCTAAGGCC | ACCCTATTTT | AATATTGGAG | GACCTTGGTG | 360 |
| AATCATACCC | AGGAAGGTAA | TTTGACCTCT | TCTCTGATCA | CCCTTATTGA | AGCCCCAAG  | 420 |
| CACCCTTCTT | GTGACAATTT | TAGGTTGGAC | CAGTTGCTTT | GGGCCAACTT | AACTAAAGTT | 480 |
| GTTCGAAAAA | CTTTTTTCCA | AAAATTTCCA | TAGGCCTCCC | AAGTTT | | 526 |

(2) INFORMATION FOR SEQ ID NO:2:

(i) SEQUENCE CHARACTERISTICS:
(A) LENGTH: 378 base pairs
(B) TYPE: nucleic acid
(C) STRANDEDNESS: single
(D) TOPOLOGY: linear (ii) MOLECULE TYPE: cDNA (vii) IMMEDIATE SOURCE:
(A) LIBRARY: U937
(B) CLONE: 1622

(xi) SEQUENCE DESCRIPTION: SEQ ID NO:2:

| | | | | | | |
|---|---|---|---|---|---|---|
| AGAACACCAC | ATCCGAGTGG | CTGACTTTGG | CAGTGCCACA | TTTGACCATG | AGCACCACAC | 60 |
| CACCATTGTG | GCCACCCGTC | ACTATCGCCG | CCTGAGGTGA | TCCTTGAGCT | GGGCTGGGCA | 120 |
| CAGCCTGGTG | ACGTCTGGGC | ATTGGCTGCA | TTCTCTTTGA | GTACTACCGG | GGCTTCACAC | 180 |
| TCTTCCAGAC | CCACGAAAAC | CGAGAGCACC | TGGTGATGAT | GGAGAAGATC | CTAGGGCCCA | 240 |
| TCCCATCACA | CATGATCCAC | CGTACCAGGA | AGCAGAATAT | TTCTACAAAG | GGGGCCTAGT | 300 |
| TTGGGATGGA | CAGCTCTTAC | GGCCGGTATG | TAAGGGACTC | AAACCTTTAA | GGTTCATGTT | 360 |
| CAAGCTTCCT | GGGAAGTG | | | | | 378 |

(2) INFORMATION FOR SEQ ID NO:3:

(i) SEQUENCE CHARACTERISTICS:
(A) LENGTH: 326 base pairs
(B) TYPE: nucleic acid
(C) STRANDEDNESS: single
(D) TOPOLOGY: linear (ii) MOLECULE TYPE: cDNA (vii) IMMEDIATE SOURCE:
(A) LIBRARY: THP-1 Phorbol LPS
(B) CLONE: 10007

(xi) SEQUENCE DESCRIPTION: SEQ ID NO:3:

| | | | | | | |
|---|---|---|---|---|---|---|
| GGGCTGGCAG | CCCGGTTGGA | GCCTCCGGAG | CAGAGGAAGA | AGACCATCTT | GGCACCCCCA | 60 |

| | | | | | |
|---|---|---|---|---|---|
| ACTATGTGGC | TCCAGAAGTG | CTGCTGAGAC | AGGGCCACGG | CCCTGAGGCG | GATGTATGGT | 120
| CACTGGGCTG | TGTCATGTAC | ACGCTGCTCT | GCGGGACCCT | CCCTTTGAGA | CGGCTGACCT | 180
| GAAGGAGACG | TACCGCTGCA | TCAAGAAGGT | TCACTACAAC | GGTGCCTGCC | AGCTCTTAAT | 240
| GCCTGCCCGA | GTCCTTGGCC | GCAATCCTTC | GGGCCTTAAC | CCGAGAACCG | GCCCTCTATT | 300
| GACAGATCCT | TGCGGCAATT | AACTTT | | | | 326

(2) INFORMATION FOR SEQ ID NO:4:

(i) SEQUENCE CHARACTERISTICS:
        (A) LENGTH: 257 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: THP-1 Phorbol LPS
        (B) CLONE: 12702

(xi) SEQUENCE DESCRIPTION: SEQ ID NO:4:

| | | | | | |
|---|---|---|---|---|---|
| CCGCAAGACA | CCTCCTGGAG | GGCCTCCTGA | GAAGGACAGG | CAAAGGGCTG | GGCCAAGGAT | 60
| GACTTCATGG | AGATTAAGAG | TCATGTTTCT | TCTCCTTAAT | TAACTGGGAT | GATCTCATTA | 120
| ATAAGAAGAT | TACTCCCCCT | TTTACCCAAA | TGTGAGTGGG | CCCAACGCCT | ACGGACTTTG | 180
| CCCCGAGTTT | ACGAAGAGCC | TTCCCCAATC | CATTGGAAGT | CCCCTGAAAG | GTCCTATACA | 240
| AGTCAGTTAA | GGAAGTT | | | | | 257

(2) INFORMATION FOR SEQ ID NO:5:

(i) SEQUENCE CHARACTERISTICS:
        (A) LENGTH: 252 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Inflamed Adenoid
        (B) CLONE: 23789

(xi) SEQUENCE DESCRIPTION: SEQ ID NO:5:

| | | | | | |
|---|---|---|---|---|---|
| GTGAAGAATG | TGGGGCTGAC | CCTCGGAAGT | CATCGGGAGC | GTGGATGATC | TCCTGCCTTC | 60
| CTTGCCGTCA | TCTCACGGAC | AGAGATCGAG | GGCACCCAGA | AACTGCTCAA | CAAAGACCTG | 120
| GCAGAGCTCA | TCAACAAGAT | GCGCTGGCGC | AAGAACGCGT | GACCTCCCTG | TAGGAGTAAG | 180
| AGGCAGATCT | GACGGTTCAC | AACCCTGGCT | GTGACGCAAG | AACCTCTTAC | GTGTGCCAGG | 240
| CCCAAAGTTC | TG | | | | | 252

(2) INFORMATION FOR SEQ ID NO:6:

(i) SEQUENCE CHARACTERISTICS:
        (A) LENGTH: 255 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Huvec
        (B) CLONE: 35652

(xi) SEQUENCE DESCRIPTION: SEQ ID NO:6:

| | | | | | |
|---|---|---|---|---|---|
| CAAAATCGTG | GCCCGGAGAA | TGGCGGGGCC | TCAACCCTCT | CCTGGACCAG | CGGCAGCTCA | 60
| CTACTCAGCT | TTTGGCCTGT | GGGCGAGTGG | CTTCGGGCCA | TCAAAATGGG | AAGATACGAA | 120
| GAAAGTTTCG | CAGCCGCTGG | CTTTGGCTCC | TTCAGCTGGT | CAGCCAGATC | TCTGCTGAGG | 180
| ACCTGCTCCG | AATCGAGTCA | CTCTGGCGGG | ACACCAGAAG | AAAATTTGGC | CAGTTCCAGC | 240
| ACATGAGTCC | CAGGT | | | | | 255

(2) INFORMATION FOR SEQ ID NO:7:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Huvec
        (B) CLONE: 35855

(xi) SEQUENCE DESCRIPTION: SEQ ID NO:7:

| | | | | | |
|---|---|---|---|---|---|
| GAATACCCCA | TATACATAGT | GACTGATATA | TAAGCAATGG | CTGCTTGCTG | AATACCTGAG | 60
| GAGTCACGGA | AAAGGCTTAA | CCTTCCCAGT | CTTAGAAATG | TGCTACGATG | TCTGTAAGGC | 120
| ATGGCCTTCT | TGGAGAGTCA | CCAATTCATA | CACCGGGCTT | GGCTGCTCGT | AACTGCTTGG | 180
| TGGACAGAGA | TCTCTGTGTG | AAAGTTCTCC | ATTTGGATGA | CAAGGTATGT | TCTTGATG | 238

(2) INFORMATION FOR SEQ ID NO:8:

(i) SEQUENCE CHARACTERISTICS:
        (A) LENGTH: 261 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: T+B Lymphoblast
        (B) CLONE: 40194

(xi) SEQUENCE DESCRIPTION: SEQ ID NO:8:

| | | | | | |
|---|---|---|---|---|---|
| AAACAACTTG | ATTATTTAGG | AATTCCTCTG | TTTTATGGAT | CTGGTCTGAC | TGAATTCAAG | 60
| GGAAGAAGTT | ACAGATTTAT | GGTAATGGAA | AGACTAGGAA | TAGATTTACA | GAAGATCTCA | 120
| GGCCAGAATG | GTACCTTTAA | AAAGTCAACT | GTCCTGCAAT | TAGGATCCGA | ATGTTGGATG | 180
| TACTGGAATA | TATACATGAA | AATGAATATG | TTCATGGTGA | TATAAAAGCA | GCAAATCTAC | 240
| TTTTGGGTTA | CAAAAATCCT | T | | | | 261

(2) INFORMATION FOR SEQ ID NO:9:

(i) SEQUENCE CHARACTERISTICS:
        (A) LENGTH: 242 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: T+B Lymphoblast
        (B) CLONE: 42170

(xi) SEQUENCE DESCRIPTION: SEQ ID NO:9:

```
TAAGAAACCT    GAAGATCGAG    CCACTGCTGA    AGAATGTCTA    AAGCACCCCT    GGTTGACACA           60

GAGCAGTATT    CAAGAGCCTT    CTTTCAGGAT    GGAAAAGGCA    CTAGAAGAAG    CAAATGCCCT          120

CCAAGAAGGT    CATTCTGTGC    CTGAAATTAA    TTCGGATACC    GACAAATCAG    AAACCGAGGA          180

ATCCATTGTA    ACCGAAGAGT    TAATTGTAGT    TACTTCATAT    ACTCTAGGGC    AATGCAGACA          240

GT                                                                                      242
```

( 2 ) INFORMATION FOR SEQ ID NO:10:

( i ) SEQUENCE CHARACTERISTICS:
        ( A ) LENGTH: 222 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Corneal Stroma
        ( B ) CLONE: 46081

( x i ) SEQUENCE DESCRIPTION: SEQ ID NO:10:

```
GCAAAGGACA    GTCCGCCGAG    GTGCTCGGTG    GAGTCATGGC    ATTCCCTTTT    GGAAGACTGG           60

CCTTGGTGCA    AACCCTGGAG    AAGGTGCCTA    TGGAGAAGTT    CAACTTGCTG    TAAATAGAGT          120

AACTAAGAAG    CAGTCGCAGT    GAAGATTTAG    ATATAAGCGT    GCCGTAGACT    GTCCCGAAAA          180

TATTAAGTAG    ATCTGTATCA    ATAAAATGCT    AATCATGAAA    TT                                222
```

( 2 ) INFORMATION FOR SEQ ID NO:11:

( i ) SEQUENCE CHARACTERISTICS:
        ( A ) LENGTH: 225 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Corneal Stroma
        ( B ) CLONE: 46651

( x i ) SEQUENCE DESCRIPTION: SEQ ID NO:11:

```
ATGCTCCGCC    AGTGAGAAGG    GCGGCTGCCT    GAGCGCCTCA    CCAGTCCTCA    TCACCCAGAT           60

CCTGTGGCTT    TGAGACACCT    TCACTTAAGA    ACATTGCCA     CTTGACTTAA    ACCAGAAACG          120

TGTTTTGTGG    CATCAGCAGA    CCCTTTCTCA    GGTAAGTTGT    GCTTTGCTTT    TAGCATACGT          180

GAGAAGTTGT    TCCGCTCCAT    TTTGTGGGAC    GTCTTTCTTT    CCTTG                             225
```

( 2 ) INFORMATION FOR SEQ ID NO:12:

( i ) SEQUENCE CHARACTERISTICS:
        ( A ) LENGTH: 256 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Fibroblast
        ( B ) CLONE: 53840

( x i ) SEQUENCE DESCRIPTION: SEQ ID NO:12:

```
CAGCGCCTTA    CATCTCGCAG    CCAAGAACAG    CCACCATGAA    TGCATCAGGA    AGCTGCTTCA           60

TCTAAATGCC    CAGCCGAAAG    TTTTGACAGC    TCTGGGAAAA    CAGCTTTACA    TTATGCAGCG          120
```

| GCTCAGGGCT | GCCTTCAAGC | TGTGCAGATT | CTTGCGAACA | CAAGAGCCCC | ATAAACCTCA | 180 |
| AAGATTTGGA | TGGGAATATA | CCGCTGCTGC | TTGCTGTACA | AAATGGTCAC | AGTGAGATCT | 240 |
| GTCACTTTTC | CTGGTC | | | | | 256 |

( 2 ) INFORMATION FOR SEQ ID NO:13:

( i ) SEQUENCE CHARACTERISTICS:
        ( A ) LENGTH: 240 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Fibroblast
        ( B ) CLONE: 54065

( x i ) SEQUENCE DESCRIPTION: SEQ ID NO:13:

| GTTGACATCT | GGTCCCTGGG | CATATGGCCA | TCGAAATGAT | TGAAGGGGAG | CCTCATACCT | 60 |
| CAATGAAAAC | CCTTGAGAGC | CTTGTACCTC | ATTGCCACCA | ATGGGACCCC | AGAACTTCAG | 120 |
| AACCCAGAGA | AGCTGTCAGC | TATCTTCCGG | GACTTTCTGA | ACCGCTGTCT | CGAGATGGAT | 180 |
| GTGGAGAAGA | GAGGTTCAGC | TAAAGAGCTG | CTACAGCATC | AATTCCTGAA | GATTGCCAAT | 240 |

( 2 ) INFORMATION FOR SEQ ID NO:14:

( i ) SEQUENCE CHARACTERISTICS:
        ( A ) LENGTH: 195 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Fibroblast
        ( B ) CLONE: 56494

( x i ) SEQUENCE DESCRIPTION: SEQ ID NO:14:

| AACAGTGAAG | AGCTCCGAGA | AATTATGGGT | ACCCTGATAT | GTGGCTCCTG | AAATTTAGTT | 60 |
| ATGATCCTAT | AAGCATGGCA | ACAGATATTG | GAGCATTGGA | GTGTTAACAT | ATGTCATGCT | 120 |
| TACAGGAATA | TCACCTTTTT | AGGCAATGAT | AAACAAGAAA | CATTCTTAAA | CATCTCACAG | 180 |
| ATGATTTTAA | GTTAT | | | | | 195 |

( 2 ) INFORMATION FOR SEQ ID NO:15:

( i ) SEQUENCE CHARACTERISTICS:
        ( A ) LENGTH: 207 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Skeletal Muscle
        ( B ) CLONE: 58029

( x i ) SEQUENCE DESCRIPTION: SEQ ID NO:15:

| GGAGTGTTTA | TCGAGCCAAA | TGGATATCAC | AGGACAAGGA | GGTGGCTGTA | AAGAAGCTCC | 60 |
| TCAAAATAGA | GAAAGAGGCA | GAAATACTCA | GTGTCCTCAG | TCACAGAAAC | ATCATCCAGT | 120 |
| TTTATGGAGT | AATTTTGAAC | CTCCCAACTA | TGGCATTGTC | ACAGAATATG | CTTCTTGGGT | 180 |

CACTCTATGA TTACATTAAC AGTACAA                                                                                   207

( 2 ) INFORMATION FOR SEQ ID NO:16:

( i ) SEQUENCE CHARACTERISTICS:
        ( A ) LENGTH: 184 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Placenta
        ( B ) CLONE: 64663

( x i ) SEQUENCE DESCRIPTION: SEQ ID NO:16:

CGGGGTGGTA AAACTTGGAG ATCTTGGGAT TGGCGGTTTT AGCTCAAAAA CCACAGCTGC            60
ACATTCTTTA GTTGGTACGC CTATTCATGT TCCAGAGGAT ACAGAAATGG ATACAACTTC          120
AAATCTCATC TGGTCTCTTG GCTGTCTACT ATATGGATGG CTGCATTACA AAGTCCTTTC          180
TATG                                                                      184

( 2 ) INFORMATION FOR SEQ ID NO:17:

( i ) SEQUENCE CHARACTERISTICS:
        ( A ) LENGTH: 206 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: HUVEC Sheer Stress
        ( B ) CLONE: 67967

( x i ) SEQUENCE DESCRIPTION: SEQ ID NO:17:

TGAATTGCTG AGCATAGACC TTTATGAGCT GATTAAAAAA AATAAGTTTC AGGTTTTAGC            60
GTCCAGTTGG TACGCAAGTT TGCCCAGTCC ATCTTGCAAT CTTTGGTGCC CTCCACAAAA          120
TAAGATTATT CACTGCGATC TGAGCCAGAA AACATTCTCC TGAAACACCA CGGGCGCAGT          180
TCAACCAAGG TCATTGACTT TGGGTT                                              206

( 2 ) INFORMATION FOR SEQ ID NO:18:

( i ) SEQUENCE CHARACTERISTICS:
        ( A ) LENGTH: 268 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: HUVEC Sheer Stress
        ( B ) CLONE: 68963

( x i ) SEQUENCE DESCRIPTION: SEQ ID NO:18:

GGGAAGTGGC CAGTTTGGAG TGGTCAGCTG GGCAAGTGGA AGGGCAGTA TGATGTTGCT            60
GTTAAGATGA TCAAGGAGGG CTCCATGTCA GAAGATGAAT TTTTCAGGAG GCCCAGACTA          120
TATGAAACTC AGCCATCCCA AGCTGGTTAA ATTCTATGGA GTGTGTTAAA GGATTACCCC          180
ATATACATGT GACTAATATA TAGCAATGCT TGCTTTTCTG AATTACCTGG GGAGTCACGG          240
AAAAAGGACT TTTAACCCTT CCCGCTTG                                            268

( 2 ) INFORMATION FOR SEQ ID NO:19:

( i ) SEQUENCE CHARACTERISTICS:
        ( A ) LENGTH: 224 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Placenta
        ( B ) CLONE: 71904

( x i ) SEQUENCE DESCRIPTION: SEQ ID NO:19:

```
CCTGGGGTGG  TAAAACTTGG  AGACTTGGCT  TGGCCGGTTT  TCCACCTCAA  AAACCACAGC      60
TGCACATCCT  TTAGTTGGTA  CGCCTTATTA  CATGTTCCAG  AGAGATACAT  GAAAATGGAT     120
ACAACTCAAA  CTGACATCTG  GCCTTTGGCT  GTTACTATAT  GAATGGCTGC  TTACAAAGCC     180
TTCCTATGGT  GACAAAATGA  TTTTACTCAT  TGTGTAAGAG  ATAG                       224
```

( 2 ) INFORMATION FOR SEQ ID NO:20:

( i ) SEQUENCE CHARACTERISTICS:
        ( A ) LENGTH: 195 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: THP-1 Phorbol
        ( B ) CLONE: 75289

( x i ) SEQUENCE DESCRIPTION: SEQ ID NO:20:

```
GCGGGGAATG  ACTCCCTATC  CTGGGGTCCA  GAACCATGAG  ATGTATGATA  TCTTCTCCAT      60
GGCCACAGGT  TGAAGCAGCC  CGAAGACTGC  CTGGTGAACT  GTATGAAATA  ATGTACTCTT     120
GCTGGAGAAC  CGATCCCTTA  GACCGCCCCA  CCTTTTCATA  TTGAGGCTGC  AGCTAGAAAA     180
ACTCTTAGAA  AGTTT                                                         195
```

( 2 ) INFORMATION FOR SEQ ID NO:21:

( i ) SEQUENCE CHARACTERISTICS:
        ( A ) LENGTH: 219 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Rheumatoid Synovium
        ( B ) CLONE: 81865

( x i ) SEQUENCE DESCRIPTION: SEQ ID NO:21:

```
CACACGAGAA  GCAGAAACAC  GACGGGCGGG  TAAGATCGGC  CACTACATTC  TGGTGACACG      60
CTGGGGGTCG  GCACCTTCGG  CAAAGTGAAG  GTTGGCAAAC  ATGATTGACT  GGCATAAAGT     120
AGCTGTAAGA  TACTCATCGA  CAGAAGATTC  GGAGCCTTGA  TGTGGTAGGA  AAAATCCCAG     180
GAAATTCAGA  ACCTCAAGCT  TTTCAGGCAT  CCTCATATA                              219
```

( 2 ) INFORMATION FOR SEQ ID NO:22:

( i ) SEQUENCE CHARACTERISTICS:
        ( A ) LENGTH: 181 base pairs
        ( B ) TYPE: nucleic acid ( C ) STRANDEDNESS: single
( D ) TOPOLOGY: linear ( i i ) MOLECULE TYPE: cDNA ( v i i ) IMMEDIATE SOURCE:
( A ) LIBRARY: HUVEC Sheer Stress
( B ) CLONE: 82056

( x i ) SEQUENCE DESCRIPTION: SEQ ID NO:22:

```
CCACCAAAGA   TCTCAAATAA   AGTTGATGTG   TGGTCGGTGG   GTGTATCTCT   ATCAGTGTCT         60
TTATGGAAGG   AAGCCTTTTG   GCCATAACCA   GTCTCAGCAA   GACATCCTAC   AAGAGAATAC        120
GATTTTAAAG   CTACTGAAGT   GCAGTTCCCG   CCAAAGCCAG   TAGTAACACC   TGAAGCAAAG        180
G                                                                                 181
```

( 2 ) INFORMATION FOR SEQ ID NO:23:

( i ) SEQUENCE CHARACTERISTICS:
( A ) LENGTH: 218 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( A ) LIBRARY: AML Blast
( B ) CLONE: 108485

( x i ) SEQUENCE DESCRIPTION: SEQ ID NO:23:

```
TATGGTTATA   TGGAAGAGAA   TGTGACTGGT   GGTCGGTTGG   GGTATTTTA    TACGAAATGC         60
TTGTAGGTGA   TACACCTTTT   TATGCAGATT   CTTTGGTTGG   AACTTACAGT   AAAATTATGA        120
ACCATAAAAA   TTCACTTACC   TTTCCTGATG   ATAATGACAT   ATCAAAAGAA   GCAAAAAACC        180
TTATTTGTGC   CTTCCTTACT   GACAGGGAAG   TGAGGTTA                                    218
```

( 2 ) INFORMATION FOR SEQ ID NO:24:

( i ) SEQUENCE CHARACTERISTICS:
( A ) LENGTH: 264 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( A ) LIBRARY: Testis
( B ) CLONE: 114973

( x i ) SEQUENCE DESCRIPTION: SEQ ID NO:24:

```
GACGGTGGCC   ATTTGACATG   TGGAGCCTGG   GTGCATCACG   GTGGAGTTGT   ACACGGGCTA         60
CCCCCTGTTC   CCCGGGAGAA   TGAGGTGGAG   CAGCTGGCCT   GCATCATGGA   GGTGCTGGGT        120
CTGCCGCCAG   CCGGCTTCAT   TCAGACAGCC   TCCAGGAGAC   AGACATTCTT   TGATTCCAAA        180
GGTTTTCCTA   AAAATATAAC   CACAACCAGG   GGAAAAAAAG   ATTCCAGATT   CCAAGGGCCC        240
TCACGGATTG   GTGCTGAAAA   AACT                                                     264
```

( 2 ) INFORMATION FOR SEQ ID NO:25:

( i ) SEQUENCE CHARACTERISTICS:
( A ) LENGTH: 236 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
    ( A ) LIBRARY: Skeltal Muscle
    ( B ) CLONE: 118591

( x i ) SEQUENCE DESCRIPTION: SEQ ID NO:25:

| | | | | | |
|---|---|---|---|---|---|
| GACTGAGGAC | ACTGAAACAT | CATCCAGTTT | TATGGAGTAA | TTCTTGAACC | TCCCAACTAT | 60
| GGCATTGTCA | CAGAATATGC | TTCTCTGGGA | TCACTCTATG | ATTACATTAA | CAGTAACAGA | 120
| AGTGAGGAGA | TGGATATGGT | CACATTATGA | CCTGGGCCAC | TGATGTAGCC | AAAGGAATGC | 180
| ATTATTTACA | TATGGGGCTC | CTGTCAAGGT | GATTCACAGA | GACCTCAAGT | CAAGGA | 236

( 2 ) INFORMATION FOR SEQ ID NO:26:

( i ) SEQUENCE CHARACTERISTICS:
        ( A ) LENGTH: 200 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Skeltal Muscle
        ( B ) CLONE: 119819

( x i ) SEQUENCE DESCRIPTION: SEQ ID NO:26:

| | | | | | |
|---|---|---|---|---|---|
| CCTGCATGGC | CTTCGAGCTG | GCCACTGGTG | ACTACCTGTT | CGAGCCGCAT | TCTGGAGAAG | 60
| ACTACAGTCG | TGATGAGGGT | AAGGGGTGAG | GGCTCTGGGC | TCAGCCTCCC | GGCCTCCGG | 120
| CCTGCCTGCC | CCCAACCTCC | TCTTTTGCCC | ACAGACCACA | TCGCTCACAT | AGTGGAGCTT | 180
| CTGGGGACA | TCCCCCCAGC | | | | | 200

( 2 ) INFORMATION FOR SEQ ID NO:27:

( i ) SEQUENCE CHARACTERISTICS:
        ( A ) LENGTH: 217 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Skeletal Muscle
        ( B ) CLONE: 120376

( x i ) SEQUENCE DESCRIPTION: SEQ ID NO:27:

| | | | | | |
|---|---|---|---|---|---|
| GATTACAAGT | AGCTTGGTTG | TAGTGGAAAA | AAACGAGAGA | TTAACCATTC | CAAGCAGTTG | 60
| CCCCAGAAGT | TTTGCTGAAC | TTTACATCAG | TTTGGGAAGC | TGATGCCAAG | AAACGGCCAT | 120
| CATTCAAGCA | AATCATTTCA | ATCCTGGGTC | CATGTCAAAT | GACACGAGCC | TTCCTGCAAG | 180
| TGTAACTCAT | TCCTACACAA | CAAGGCGGAG | TGGAGGT | | | 217

( 2 ) INFORMATION FOR SEQ ID NO:28:

( i ) SEQUENCE CHARACTERISTICS:
        ( A ) LENGTH: 156 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Bone Marrow
        ( B ) CLONE: 132750

( x i ) SEQUENCE DESCRIPTION: SEQ ID NO:28:

GTAGATTTGA CTCTGTTGTT TTCTCTCGTA GTTCCCAAAC TCATGGAAGT CTGTTTTTAT  60

CAATATGATG TAAAGTCTGA AATATACAGC TTTGGAATCG TCCTCTGGGA AATCGCCACT  120

GGAGATATCC CGTTTCAAGG CTGTAATTCT GAGAAG  156

( 2 ) INFORMATION FOR SEQ ID NO:29:

( i ) SEQUENCE CHARACTERISTICS:
        ( A ) LENGTH: 224 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: T Lymphocyte
        ( B ) CLONE: 140052

( x i ) SEQUENCE DESCRIPTION: SEQ ID NO:29:

TGTAAATAAG GCCCTTCTCC ACTTGACTTC AGGCAGCAGA TTGTCTAGAA GCCTAAGGAC  60

AGCAATTTCT CTGACAAGAC AAAGTAGATA TTTTATACCA GGGGTTGGCA AACTACTGCC  120

CACGGGCCGA ATTTGGCCCA GTCTGTTTTT GTATGGTGCA AACTAAAAAT GATTTTACA  180

TTTTTAAAGA GTTATAAAAG AAAAAAATAT GTGGTCTGTG AAAT  224

( 2 ) INFORMATION FOR SEQ ID NO:30:

( i ) SEQUENCE CHARACTERISTICS:
        ( A ) LENGTH: 198 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: T Lymphocyte
        ( B ) CLONE: 146392

( x i ) SEQUENCE DESCRIPTION: SEQ ID NO:30:

TTTTCTTTGT GTTTTTTTTT GTTCCAGTTT ATTTAAATG CATATTTTAG TTGATTGCTT  60

TTTTAAAAAG CCCCCTCTGG CCTCCTGATT CCAGCTAGTG TCAGCAGTGG GATACCTGCG  120

CTTGAAGGAC ATCATCCACC GTGACATCAA GGATGAGAAC ATCGTGATCG CCGAGGACTT  180

CACAATCAAG CTGATAGT  198

( 2 ) INFORMATION FOR SEQ ID NO:31:

( i ) SEQUENCE CHARACTERISTICS:
        ( A ) LENGTH: 210 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: THP-1 Phorbol LPS
        ( B ) CLONE: 156108

( x i ) SEQUENCE DESCRIPTION: SEQ ID NO:31:

TGAAAACTAT GAACCTGGAC AAAAATCAAG GGCCAGTATC AAGCACGATA TATATAGCTA  60

TGCAGTTATC ACATGGGAAG TGTTATCCAG AAAACAGCCT TTTGAAGATG TCACCAATCC  120

```
TTTGCAGATA   ATGTATAGTG   TGTCACAAGG   ACATCGACCT   GTTATTAATG   AAGAAAGTTT        180

GCCATATGAT   ATACCTCACC   GAGCACGTAT                                               210
```

( 2 ) INFORMATION FOR SEQ ID NO:32:

( i ) SEQUENCE CHARACTERISTICS:
        ( A ) LENGTH: 202 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Bone Marrow
        ( B ) CLONE: 173627

( x i ) SEQUENCE DESCRIPTION: SEQ ID NO:32:

```
AGAAGATCGG   GGCCGGCTTC   TTCTCTGAGG   TCTACAAGGT   TCGGCACCGA   CAGTCAGGGC         60

AAGTATGGTG   CTGAAGATGA   ACAAGCTCCC   CAGTAACCGG   GGCAACACAC   TACGGGAAGT        120

GCAGCTGATG   AACCGGCTCA   GGCACCCCAA   CATCCTAAGG   TTCATGGGAG   TCTGTGTGCA        180

CCAGGGACAG   CTGCACGCTC   TT                                                      202
```

( 2 ) INFORMATION FOR SEQ ID NO:33:

( i ) SEQUENCE CHARACTERISTICS:
        ( A ) LENGTH: 222 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Placenta
        ( B ) CLONE: 181971

( x i ) SEQUENCE DESCRIPTION: SEQ ID NO:33:

```
CGTTTTTGGA   GGGTTCACAC   CTGTCCCTTT   CAAATGCTGG   CGCTTTCACA   CACTCCTTCT         60

CTCCTGCCAG   CACCTTCTGG   TCTCAGGAGC   ATTGCAGGAT   GTTGTGTGAG   TAAGTATGGG        120

AGACACTTTA   GTATGGCTTT   TTTCAGCTTA   GCCTCCTGTT   ATCAGAGAGC   AGTCTCTTTC        180

AGTGTCAAGG   TTTGAGTACT   AGATGGTGGA   GAAAGCCTGT   TT                            222
```

( 2 ) INFORMATION FOR SEQ ID NO:34:

( i ) SEQUENCE CHARACTERISTICS:
        ( A ) LENGTH: 192 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Placenta
        ( B ) CLONE: 182538

( x i ) SEQUENCE DESCRIPTION: SEQ ID NO:34:

```
CTTGGGGTGG   TAAAACTTGG   AGATCTTGGG   CTTGGCCGGT   TTTTCAGCTC   AAAAACCACA         60

GCTGCACATT   CTTTAGTTGG   TACGCCTTAT   TACATGTCTC   CAGAGAGAAT   ACATGAAAAT        120

GGATACAACT   TCAAATCTGA   CATCTGGTCT   CTTGGCTGTC   TACTATATGA   GATGGCTGCA        180

TTACAAAGTC   CT                                                                   192
```

( 2 ) INFORMATION FOR SEQ ID NO:35:

( i ) SEQUENCE CHARACTERISTICS:
        ( A ) LENGTH: 152 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Cardiac Muscle
        ( B ) CLONE: 184416

( x i ) SEQUENCE DESCRIPTION: SEQ ID NO:35:

```
CTATGGAAGG  CCGCTGGCAG  GGCAATGACA  TTGTCGTGAA  GGTGCTGAAG  GTTCGAGACT       60
GGAGTACAAG  GAAGAGCAGG  GACTTCAATG  AAGAGTGTCC  CCGGCTCAGG  ATTTTTCGCA      120
TCCAAATGTG  CTCCCAGTGC  TAGGTGCCTG  CC                                     152
```

( 2 ) INFORMATION FOR SEQ ID NO:36:

( i ) SEQUENCE CHARACTERISTICS:
        ( A ) LENGTH: 152 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Rheumatoid Synovium
        ( B ) CLONE: 191283

( x i ) SEQUENCE DESCRIPTION: SEQ ID NO:36:

```
CAACTACAGT  GAACCTAAAA  TGCCTCTAAT  ACCTTTGCAA  TTATCTTTAA  GAGGATATCT       60
TATGAGTGAA  ATTAACTTGT  GCAACTACTT  TCCTATTCAC  TTTTTTACAG  AGACTTAAAA      120
CCAGAGAATA  TTTCTAGATT  CACAGGGACA  CT                                     152
```

( 2 ) INFORMATION FOR SEQ ID NO:37:

( i ) SEQUENCE CHARACTERISTICS:
        ( A ) LENGTH: 199 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Rheumatoid Synovium
        ( B ) CLONE: 192268

( x i ) SEQUENCE DESCRIPTION: SEQ ID NO:37:

```
AGTGGACTGC  AGTAAGCAGA  GCTTCCTGAC  CGAGGTGGAG  CAGCTGTCCA  GGTTTCGTCA       60
CCCAAACATT  GTGGACTTTC  TGGCTACTGT  GCTCAGAACG  GCTTCTACTG  CCTGGTGTAC      120
GGCTTCCTGC  CCAACGGCTC  CCTGGAGGAC  CGTTCCACTG  CCAGACCCAG  GCCTGCCCAC      180
CTCTCTCCTG  GCCTCAGCG                                                      199
```

( 2 ) INFORMATION FOR SEQ ID NO:38:

( i ) SEQUENCE CHARACTERISTICS:
        ( A ) LENGTH: 189 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
      ( A ) LIBRARY: Stomach
      ( B ) CLONE: 214915

( x i ) SEQUENCE DESCRIPTION: SEQ ID NO:38:

| | | | | | |
|---|---|---|---|---|---|
| AGAAGATCCA | GTACCTGGTG | TATCAATGCT | CAAAGGCCTT | AAGTACATCC | ACTCTCTGGG | 60
| GTCGTGCACA | GGGACCTGAA | GCCAGGCAAC | CTGGCTGTGA | ATAGGACTGT | AACTGAAGAT | 120
| TCTGGATTTT | GGGCTGGCGC | GACATGCAGA | CGCCGAGATG | ACTGGCTACG | TGGTGACCCG | 180
| CTGGTACCT | | | | | | 189

( 2 ) INFORMATION FOR SEQ ID NO:39:

( i ) SEQUENCE CHARACTERISTICS:
      ( A ) LENGTH: 167 base pairs
      ( B ) TYPE: nucleic acid
      ( C ) STRANDEDNESS: single
      ( D ) TOPOLOGY: linear ( i i ) MOLECULE TYPE: cDNA ( v i i ) IMMEDIATE SOURCE:
      ( A ) LIBRARY: Pancreas
      ( B ) CLONE: 223163

( x i ) SEQUENCE DESCRIPTION: SEQ ID NO:39:

| | | | | | |
|---|---|---|---|---|---|
| CTTGCTCTTC | TGACAGGATG | AGAGTTATTA | TAAGCAAATC | CTACCTAGAG | GCTTTTAACT | 60
| CTAATGGGAA | TAACTTGCAA | CTAAAAGACC | CAACTTGCAG | ACCAAAATTA | TCAAATGTTG | 120
| TGGATTTTCT | GTCCCTCTTA | ATGGATGTGG | TACAATCAGA | AAGGTAG | | 167

( 2 ) INFORMATION FOR SEQ ID NO:40:

( i ) SEQUENCE CHARACTERISTICS:
      ( A ) LENGTH: 197 base pairs
      ( B ) TYPE: nucleic acid
      ( C ) STRANDEDNESS: single
      ( D ) TOPOLOGY: linear ( i i ) MOLECULE TYPE: cDNA ( v i i ) IMMEDIATE SOURCE:
      ( A ) LIBRARY: Small Intestine
      ( B ) CLONE: 237002

( x i ) SEQUENCE DESCRIPTION: SEQ ID NO:40:

| | | | | | |
|---|---|---|---|---|---|
| CCCAAACCTG | CCCAGCCAGC | CCTGAAAATG | CAAGTTTTGT | ACGATTTTGA | AGCTAGGAAC | 60
| CCACGGGAAC | TGACTGTGGT | CCAGGGAGAG | AAGCTGGAGG | TTTGGACCAC | AGCAAGCGGT | 120
| GGTGGCTGGT | GAAGAATAGG | CGGGACGGAG | CGGCTACATT | CCAAGCAACA | TCTGGGCCCC | 180
| TACAGCCGGG | GACCCCG | | | | | 197

( 2 ) INFORMATION FOR SEQ ID NO:41:

( i ) SEQUENCE CHARACTERISTICS:
      ( A ) LENGTH: 207 base pairs
      ( B ) TYPE: nucleic acid
      ( C ) STRANDEDNESS: single
      ( D ) TOPOLOGY: linear ( i i ) MOLECULE TYPE: cDNA ( v i i ) IMMEDIATE SOURCE:
      ( A ) LIBRARY: Hippocampus
      ( B ) CLONE: 239990

( x i ) SEQUENCE DESCRIPTION: SEQ ID NO:41:

| | | | | | | |
|---|---|---|---|---|---|---|
| CCAAGATGCT | GGAGGAACTC | AAGCCGAGAC | TTGTACCAAG | GAGAGATGAG | CAGGAAGGAG | 60 |
| GCAGAGGGCT | CTGAGAAAGA | CGGGACTTCC | TGGTCAGGAA | GAGCACCACC | AACCCGGGCT | 120 |
| CCTTTTCCTC | ACGGGCATGC | ACAATGGCCA | GGCAAGCACC | TGCTGCTCTT | GGACCCAGAA | 180 |
| GGCACGTCCG | GACAAAGGCA | GAGTCTT | | | | 207 |

(2) INFORMATION FOR SEQ ID NO:42:

(i) SEQUENCE CHARACTERISTICS:
  (A) LENGTH: 195 base pairs
  (B) TYPE: nucleic acid
  (C) STRANDEDNESS: single
  (D) TOPOLOGY: linear (i i) MOLECULE TYPE: cDNA (v i i) IMMEDIATE SOURCE:
  (A) LIBRARY: Hippocampus
  (B) CLONE: 240142

(x i) SEQUENCE DESCRIPTION: SEQ ID NO:42:

| | | | | | | |
|---|---|---|---|---|---|---|
| GTCACCGGAG | AGGATCCATG | AGAACGGCTA | CAACTTCAAG | TCCGACATCT | GGTCCTTGGG | 60 |
| CTGTCTGCTG | TACGAGATGG | CAGCCCTCCA | GAGCCCCTTC | TATGGAGATA | AGATGAATCT | 120 |
| TTCTCCCTGT | GCCAGAAGAT | CGAGCAGTGT | GACTACCCCC | CACTCCCCGG | GGAGCACTAC | 180 |
| TCCGAGAAGT | TACGT | | | | | 195 |

(2) INFORMATION FOR SEQ ID NO:43:

(i) SEQUENCE CHARACTERISTICS:
  (A) LENGTH: 213 base pairs
  (B) TYPE: nucleic acid
  (C) STRANDEDNESS: single
  (D) TOPOLOGY: linear (i i) MOLECULE TYPE: cDNA (v i i) IMMEDIATE SOURCE:
  (A) LIBRARY: Testes
  (B) CLONE: 275781

(x i) SEQUENCE DESCRIPTION: SEQ ID NO:43:

| | | | | | | |
|---|---|---|---|---|---|---|
| CTCGTCTATT | CGGCACGAGT | TTCATTGTCG | AAGGAAATAT | AAACTGTCTG | GAAGATCTGG | 60 |
| TGTAGCTCCT | TCGAGACATC | TTTGGCGATC | AGCATCACCA | ACGGTAAGAA | GTGTAGTAAG | 120 |
| CCAGATCTCA | GGGCCAGGCA | TCCCCAGTTG | CTGTACAAGA | GCAGGCTTTC | AAGATGCTTC | 180 |
| AAGGTCCCTG | TCCATCAATA | TGCTACACAT | TTG | | | 213 |

(2) INFORMATION FOR SEQ ID NO:44:

(i) SEQUENCE CHARACTERISTICS:
  (A) LENGTH: 425 base pairs
  (B) TYPE: nucleic acid
  (C) STRANDEDNESS: single
  (D) TOPOLOGY: linear (i i) MOLECULE TYPE: cDNA (v i i) IMMEDIATE SOURCE:
  (A) LIBRARY: Eosinophils
  (B) CLONE: 285465

(x i) SEQUENCE DESCRIPTION: SEQ ID NO:44:

| | | | | | | |
|---|---|---|---|---|---|---|
| AAATACTTGA | AGGAGTTTAT | TATCTACATC | AGAATAACAT | TGTACACCTT | GATTTAAAGC | 60 |
| CACAGAATAT | ATTACTGAGC | AGCATATACC | CTCTCGGGGA | CATTAAAATA | GTAGATTTTG | 120 |
| GAATGTCTCG | AAAAATAGGG | CATGCGTGTG | AACTTCGGGA | AATCATGGGA | ACACCAGAAT | 180 |

-continued

| | | | | | |
|---|---|---|---|---|---|
| ATTTAGCTCC | AGAAATCCTG | AACTATGATC | CCATTACCAC | AGCAACAGAT | ATGTGGAATA | 240 |
| TTGGTATAAT | AGCATATATG | TTGTTAACTC | ACACATCACC | ATTTGTGGGA | GAAGATAATC | 300 |
| AAGAAACATA | CCTCAATATC | TCTCAAGTTA | ATGTAGATTA | TTCGGAAGGA | ACTTTTTCAT | 360 |
| CAGTTTCACA | GCTGGCACAG | ACTTTATTCA | GAGCTTTTAG | TAAAATCAGA | GGAAAGGCCC | 420 |
| ACAGC | | | | | | 425 |

( 2 ) INFORMATION FOR SEQ ID NO:45:

( i ) SEQUENCE CHARACTERISTICS:
    ( A ) LENGTH: 1851 base pairs
    ( B ) TYPE: nucleic acid
    ( C ) STRANDEDNESS: single
    ( D ) TOPOLOGY: linear ( i i ) MOLECULE TYPE: cDNA ( v i i ) IMMEDIATE SOURCE:
    ( A ) LIBRARY: Stomach
    ( B ) CLONE: 214915E ( x i ) SEQUENCE DESCRIPTION: SEQ ID NO:45:

| | | | | | |
|---|---|---|---|---|---|
| GCCCGTTGGG | CCGCGAACGC | AGCCGCCACG | CCGGGGCCGC | CGAGATCGGG | TGCCCGGGAT | 60 |
| GAGCCTCATC | CGGAAAAAGG | GCTTCTACAA | GCAGGACGTC | AACAAGACCG | CCTGGGAGCT | 120 |
| GCCCAAGACC | TACGTGTCCC | CGACGCACGT | CGGCAGCGGG | GCCTATGGCT | CCGTGTGCTC | 180 |
| GGCCATCGAC | AAGCGGTCAG | GGGAGAAGGT | GGCCATCAAG | AAGCTGAGCC | GACCCTTTCA | 240 |
| GTCCGAGATC | TTCGCCAAGC | GCGCCTACCG | GGAGCTGCTG | TTGCTGAAGC | ACATGCAGCA | 300 |
| TGAGAACGTC | ATTGGGCTCC | TGGATGTCTT | CACCCCAGCC | TCCTCCCTGG | AACTTCTATG | 360 |
| ACTTCTACCT | GGTGATGCCC | TTCATGCAGA | CGGATCTGCA | GAAGATCATG | GGGATGGAGT | 420 |
| TCAGTGAGGA | GAAGATCCAG | TACCTGGTGT | ATCAGATGCT | CAAAGGCCTT | AAGTACATCC | 480 |
| ACTCTGCTGG | GGTCGTGCAC | AGGGACCTGA | AGCCAGGCAA | CCTGGCTGTG | AATGAGGACT | 540 |
| GTGAACTGAA | GATTCTGGAT | TTGGGGCTGG | CGCGACATGC | AGACGCCGAG | ATGACTGGCT | 600 |
| ACGTGGTGAC | CCGCTGGTAC | CGAGCCCCCG | AGGTGATCCT | CAGCTGGATG | CACTACAACC | 660 |
| AGACAGTGGA | CATCTGGTCT | GTGGGCTGTA | TCATGGCAGA | GATGCTGACA | GGGAAAACTC | 720 |
| TGTTCAAGGG | GAAAGATTAC | CTGGACCAGC | TGACCCAGAT | CCTGAAAGTG | ACCGGGGTGC | 780 |
| CTGGCACGGA | GTTTGTGCAG | AAGCTGAACG | ACAAAGCGGC | CAAATCCTAC | ATCCAGTCCC | 840 |
| TGCCACAGAC | CCCCAGGAAG | GATTTCACTC | AGCTGTTCCC | ACGGGCCAGC | CCCCAGCCTG | 900 |
| CGGACCTGCT | GGAGAAGATG | CTGGAGCTAG | ACGTGGACAA | GCGCCTGACG | GCCGCGCAGG | 960 |
| CCCTCACCCA | TCCCTTCTTT | GAACCCTTCC | GGGACCCTGA | GGAAGAGACG | GAGGCCCAGC | 1020 |
| AGCCGTTTGA | TGATTCCTTA | GAACACGAGA | AACTCACAGT | GGATGAATGG | AAGCAGCACA | 1080 |
| TCTACAAGGA | GATTGTGAAC | TTCAGCCCCA | TTGCCCGGAA | GGACTCACGG | CGCCGGAGTG | 1140 |
| GCATGAAGCT | GTAGGGACTC | ATCTTGCATG | GCACCGCCGG | CCAGACACTG | CCCAAGGACC | 1200 |
| AGTATTTGTC | ACTACCAAAC | TCAGCCCTTC | TTGGAATACA | GCCTTTCAAG | CAGAGGACAG | 1260 |
| AAGGGTCCTT | CTCCTTATGT | GGGAAATGGG | CCTAGTAGAT | GCAGAATTCA | AGATGTCGG | 1320 |
| TTGGGAGAAA | CTAGCTCTGA | TCCTAACAGG | CCACGTTAAA | CTGCCCATCT | GGAGAATCGC | 1380 |
| CTGCAGGTGG | GGCCCTTTCC | TTCCCGCCAG | AGTGGGGCTG | AGTGGGCGCT | GAGCCAGGCC | 1440 |
| GGGGGCCTAT | GGCAGTGATG | CTGTGTTGGT | TTCCTAGGGA | TGCTCTAACG | AATTACCACA | 1500 |
| AACCTGGTGG | ATTGAAACAG | CAGAACTTGA | TTCCCTTACA | GTTCTGGAGG | CTGGAAATCT | 1560 |

| | | | | | | |
|---|---|---|---|---|---|---|
| GGGATGGAGG | TGTTGGCAGG | GCTGTGGTCC | CTTTGAAGGC | TCTGGGGAAG | AATCCTTCCT | 1620 |
| TGGCTCTTTT | TAGCTTGTGG | CGGCAGTGGG | CAGTCCGTGG | CATTCCCCAG | CTTATTGCTG | 1680 |
| CATCACTCCA | GTCTCTGTCT | CTTCTGTTCT | CTCCTCTTTT | AACAACAGTC | ATTGGATTTA | 1740 |
| GGGCCCACCC | TAATCCTGTG | TGATCTTATC | TTGATCCTTA | TTAATTAAAC | CTGCAAATAC | 1800 |
| TCTAGTTCCA | AATAAAGTCA | CATTCTCAGG | TAAAAAAAAA | AAAAAAAAA | A | 1851 |

We claim:

1. A purified polynucleotide having a nucleic acid sequence selected from the group consisting of SEQ ID NO:1, SEQ ID NO:2, SEQ ID NO:3, SEQ ID NO: 4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, and SEQ ID NO:44.

2. An expression vector comprising the polynucleotide of claim 1.

3. A host cell transformed with the expression vector of claim 2.

4. A method for producing and purifying a polypeptide, said method comprising the steps of:
   a) culturing the host cell of claim 3 under conditions suitable for the expression of the peptide; and
   b) recovering the polypeptide from the host cell culture.

* * * * *